(12) United States Patent
Skelton et al.

(10) Patent No.: US 8,708,934 B2
(45) Date of Patent: Apr. 29, 2014

(54) REORIENTATION OF PATIENT POSTURE STATES FOR POSTURE-RESPONSIVE THERAPY

(75) Inventors: Dennis M. Skelton, Bloomington, MN (US); John P. Davis, St. Michael, MN (US); Dennis Bourget, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 916 days.

(21) Appl. No.: 12/433,623

(22) Filed: Apr. 30, 2009

(65) Prior Publication Data

US 2010/0010383 A1     Jan. 14, 2010

Related U.S. Application Data

(60) Provisional application No. 61/080,106, filed on Jul. 11, 2008.

(51) Int. Cl.
*A61B 5/00* (2006.01)

(52) U.S. Cl.
USPC .......................................................... 600/595

(58) Field of Classification Search
USPC ........................... 600/587, 595; 702/150, 153
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Max Hindenburg
(74) *Attorney, Agent, or Firm* — Shumaker & Sieffert, P.A.

(57) ABSTRACT

In general, the disclosure relates to medical devices and systems configured to deliver posture-responsive therapy to a patient. For example, a medical system may detect a posture state of a patient and deliver therapy based at least in part on the detected patient posture state. In some examples, the system comprises a posture state sensor configured to generate first posture sensor data when a patient is in a first posture state. The system may further comprise a processor configured to define posture state reference data corresponding to the first posture state based at least in part on the first posture sensor data, and redefine the posture state reference data based on second posture data generated by the posture state sensor when the patient is in the first posture state.

50 Claims, 17 Drawing Sheets

(56) References Cited

U.S. PATENT DOCUMENTS

| | | |
|---|---|---|
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,469,861 A * | 11/1995 | Piscopo et al. ............... 600/594 |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,833,713 A * | 11/1998 | Moberg ........................ 607/19 |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A * | 3/2000 | Sheldon et al. ............... 607/17 |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. ............... 607/14 |
| 7,181,281 B1 * | 2/2007 | Kroll ............... 607/14 |
| 7,189,204 B2 | 3/2007 | Ni et al. |

(56) References Cited

U.S. PATENT DOCUMENTS

| | | |
|---|---|---|
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn et al. |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1* | 5/2007 | Wang et al. .................. 600/595 |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |

(56) References Cited

U.S. PATENT DOCUMENTS

| | | |
|---|---|---|
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

(56) References Cited

OTHER PUBLICATIONS

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, 9$^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9$^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/49180: International Search Report and Written Opinion, dated Oct. 1, 2009, 14 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

REORIENTATION OF PATIENT POSTURE STATES FOR POSTURE-RESPONSIVE THERAPY

This application claims the benefit of U.S. Provisional Application No. 61/080,106, titled, "REORIENTATION OF PATIENT POSTURE STATES FOR POSTURE-RESPONSIVE THERAPY," and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure relates to medical devices configured to deliver posture-responsive therapy to a patient. A medical device may detect a posture state of a patient and deliver therapy based at least in part on the detected patient posture state. For example, the medical device may adjust one or more therapy parameter values or other characteristics of the therapy based on the detected posture state.

A posture state may refer to a patient posture or a combination of posture and activity. Various posture states may be defined, at least in part, by different sets of posture state reference data. In some examples, posture sensor data received from a posture state sensor when a patient occupies a particular posture state may be used to define, at least in part, posture state reference data corresponding to the respective posture state. The posture state reference data for a posture state may define, for example, a reference coordinate vector and a region around the reference coordinate vector. In some cases, the region may include a range of coordinates within a predetermined distance from the vector. In operation, a posture sensor module associated with the medical device compares posture sensor data to the posture state reference data to detect the posture occupied by the patient.

It may be desirable to redefine the posture state reference data to, in effect, reorient a posture sensor relative to the patient. In some examples, existing therapy information associated with previously defined posture state reference data may be associated with newly redefined posture state reference data, thereby avoiding the need to reacquire or reset all of the therapy information. Examples of therapy information may include therapy parameter settings, therapy-related statistics, or other information relating to the posture-responsive therapy.

In one example, the disclosure relates to a method comprising receiving first posture sensor data from a posture state sensor when a patient is in a first posture state; defining posture state reference data corresponding to the first posture state based at least in part on the first posture sensor data; and redefining the posture state reference data based on second posture sensor data from the posture state sensor when the patient is in the first posture state.

In another example, the disclosure relates to a system comprising a posture state sensor configured to generate first posture sensor data when a patient is in a first posture state; and a processor configured to define posture state reference data corresponding to the first posture state based at least in part on the first posture sensor data, and redefine the posture state reference data based on second posture data generated by the posture state sensor when the patient is in the first posture state.

In another example, the disclosure relates to a computer-readable storage medium comprising instructions to cause one or more processors to receive first posture sensor data from a posture state sensor when a patient is in a first posture state; define posture state reference data corresponding to the first posture state based at least in part on the first posture sensor data; and redefine the posture state reference data based on second posture sensor data from the posture state sensor when the patient is in the first posture state.

In another example, the disclosure relates to a system comprising means for receiving first posture sensor data from means for sensing posture state data when a patient is in a first posture state; means for defining posture state reference data corresponding to the first posture state based at least in part on the first posture sensor data; and means for redefining the posture state reference data based on second posture sensor data from the posture state sensor when the patient is in the first posture state.

The details of one or more examples of the invention are set forth in the accompanying drawings and the description below. Other features, objects, and advantages of the invention will be apparent from the description and drawings, and from the claims.

DETAILED DESCRIPTION

Figure 1A:
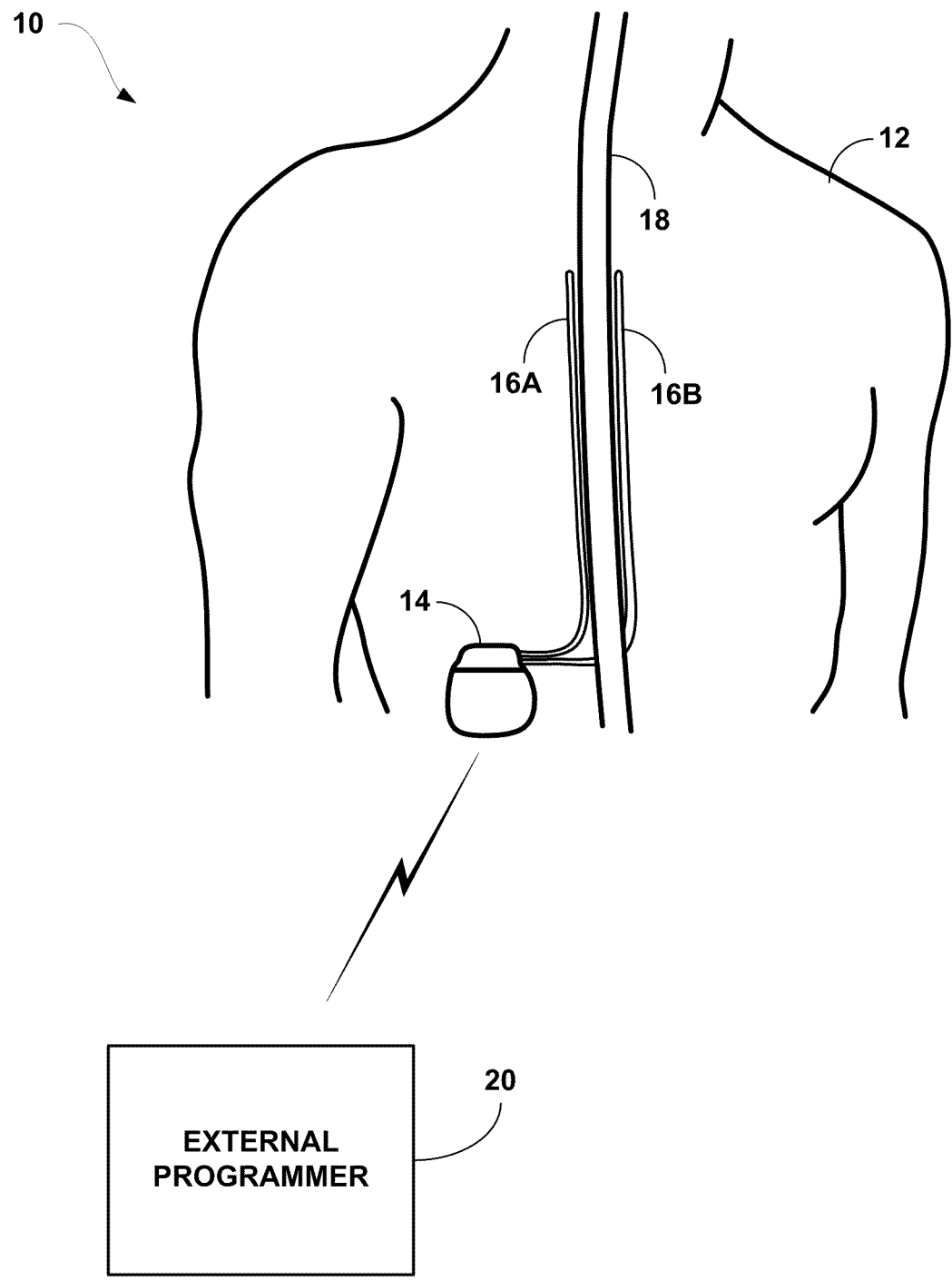
FIG. 1A is a conceptual diagram illustrating an example implantable stimulation system including two implantable stimulation leads.

In some medical devices that deliver electrical stimulation therapy, therapeutic efficacy may change as the patient changes posture states. In general, a posture state may refer to a patient posture or a combination of posture and activity. For example, some posture states, such as upright, may be subcategorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A therapy system may adjust therapy by modifying values for one or more therapy parameters, e.g., by specifying adjustments to a specific therapy parameter or by selecting different therapy programs or groups of programs that define different sets of therapy parameter values.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device employs a posture state module that detects the patient posture state. The medical device adjusts therapy parameters in response to different posture states, which are determined with the posture state module. Therapy adjustments in response to different posture states may be fully automatic, semi-automatic in the sense that a user may provide approval of proposed changes, or user-directed in the sense that the patient may manually adjust therapy based on the posture state indication.

In general, the disclosure relates to medical devices configured to deliver posture-responsive therapy to a patient. A medical device may detect a posture state of a patient and deliver therapy based at least in part on the detected patient posture state. For example, the medical device may adjust one or more therapy parameter values or other characteristics of the therapy based on the detected posture state.

A posture state may refer to a patient posture or a combination of posture and activity. Various posture states may be defined, at least in part, by different sets of posture state reference data. In some examples, posture sensor data received from a posture state sensor when a patient occupies a particular posture state may be used to define, at least in part, posture state reference data corresponding to the respective posture state. The posture state reference data for a posture state may define, for example, a reference coordinate vector and a region around the reference coordinate vector. For example, the region around the reference coordinate vector may include a range of coordinates within a predetermined distance from the reference coordinate vector. In operation, a posture sensor module associated with the medical device compares posture sensor data to the posture state reference data to detect the posture occupied by the patient.

It may be desirable to redefine the posture state reference data to, in effect, reorient a posture sensor relative to the patient. In some examples, existing therapy information associated with previously defined posture state reference data may be associated with newly redefined posture state reference data, thereby avoiding the need to reacquire or reset all of the therapy information. Examples of therapy information may include therapy parameter settings, therapy-related statistics, or other information relating to the posture-responsive therapy. In some case, the therapy information may include adjustments to the posture state reference data made prior to redefining the posture state reference data. For example, the therapy information may include any modifications to any distance(s) or angle(s) defined with respect to a reference coordinate vector to modify, e.g., increase or decrease, the region or regions around the reference coordinate vector that define the range of coordinates associated with the respective vector. As another example, the therapy information may include any modifications to cosine value(s) or cosine value range(s) defined with respect to a reference coordinate vector to modify the region or regions around the reference coordinate vector that define the range of vector coordinates associated with the respective vector. By associating these prior adjustments to the redefined posture state reference data, substantially the same adjustments may be applied to the redefined posture state reference data.

A medical device may deliver one or more types of therapy to patient, including electrical stimulation therapy and/or non-electrical stimulation therapy, such as therapeutic fluid delivery therapy. For purposes of illustration, the examples in this disclosure will be described with respect to the delivery of electrical stimulation therapy. However, it is understood that, in some examples, the same or similar principles may be applicable to the delivery of non-electrical stimulation therapy.

A medical device, such as an IMD, may deliver electrical stimulation therapy to a patient for a variety of reasons. For example, an IMD may deliver electrical stimulation therapy to treat patients that suffer from chronic back pain, leg pain, or other pain that cannot be effectively or efficiently treated through other methods. Generally, values for one or more stimulation parameters associated with the electrical stimulation therapy can be defined to treat one or more of the conditions experienced by a patient. However, as a patient changes posture states, which may include changes in posture and/or activity level, the stimulation therapy delivered by the IMD to the patient may have to be adjusted to maintain therapeutic efficiency.

In some examples, an IMD detects changes in the posture state of a patient and automatically modifies the stimulation therapy being delivered to the patient based on the detected posture state change so as to maintain effective therapeutic results. As one example, an IMD may adjust the values of one or more stimulation parameters of the stimulation therapy being delivered to a patient, e.g., stimulation amplitude value, to values that have been correlated to the posture state detected by the IMD for the patient. When a patient transitions from an upright to a lying posture, for example, the IMD may adjust the stimulation amplitude value from a value appropriate for the upright posture to a different value appropriate for the lying posture.

A medical device, such as an IMD, may utilize a posture state module, which may include a posture state sensor, to detect the posture state of a patient. As an example, to detect the posture state of a patient, a posture state module may receive posture sensor data generated by the posture state sensor and compare the posture sensor data to posture state reference data. The posture sensor data may comprise a three-dimensional coordinate vector. The posture state reference data may define a three-dimensional reference coordinate vector and a range of coordinates within a predetermined distance from the reference coordinate vector. In such a case, the posture state reference data may, in effect, define a posture volume, such as, e.g., a posture cone. The posture cone, and the range of vector coordinates within the cone, may be defined in a variety of ways. For example, the posture cone may be defined by a distance or angle relative to the reference coordinate vector. As an alternative, a range of cosine values may define vectors within the cone in the sense that a cosine value computed for each of the vectors in the cone and the reference coordinate vector falls within the range of cosine values.

If the posture sensor data falls within the range of coordinates defined by the posture state reference data, the IMD determines that the patient occupies the posture state associated with the posture state reference data. Different posture states are associated with different sets of posture state reference data. If the coordinates indicated by posture sensor data falls within the range of posture coordinates specified by the posture state reference data corresponding to an upright posture state, for example, then the IMD may detect that the patient is in the upright posture state. The posture sensor data may be compared to multiple sets of posture state reference data until a matching posture state is detected. In some examples, however, posture sensor data may fall within undefined areas that do not match any posture state reference data.

To support posture state detection, a posture sensor associated with the IMD may initially need to be oriented. For example, the posture state reference data corresponding to particular posture states may not be known with respect to the actual posture state of a patient. At that time, while an IMD may receive a signal from a posture state sensor when a patient in a particular posture state, the IMD may not be able to determine what posture state is indicated by the posture state sensor data because posture state reference data has not yet been defined for the particular posture state.

Consequently, one or more steps may be taken to orient the posture state sensor with respect to the patient's posture states. To orient the posture state sensor and postures state module to the patient, different sets of posture state reference data may be defined for the different posture states of a patient. Following orientation, the posture sensor module may use the posture state reference data to detect posture states based on posture sensor data.

As one example, as will be described in greater detail below, to define a set of posture state reference data for a particular posture state, a patient may occupy the posture state. While the patient occupies the posture state, the posture state may be communicated to the IMD, e.g., from an external programmer via wireless telemetry. Then, the IMD may define posture state reference data for the posture state based on the posture sensor data obtained from the posture state sensor while the patient is in the indicated posture state. In this manner, the IMD may define a set of posture state reference data based on the posture sensor data that is actually produced while the patient is in the respective posture state.

Once posture state reference data is defined for a posture state, the IMD may detect when a patient is occupying that posture state based on a comparison of the posture sensor data to the posture state reference data for the posture state. If there is a match between the posture sensor data generated by the posture state sensor and the posture state reference data, then the IMD detects the patient is in the pertinent posture state. The orientation process may be repeated for each of the posture states of the patient that are desired to be detected, or for a subset of the posture states sufficient to determine posture state reference data for all posture states.

In some examples, the IMD associates therapy information with a posture state. For example, an IMD may be configured to deliver stimulation therapy as defined by one or more stimulation programs that are associated with the posture state detected by IMD. An IMD may store a look-up table or other data structure that contains records, in which each record contains therapy information associated with the respective posture state. These programs may define different stimulation parameter values that provide effective stimulation therapy to a patient when they are in the respective posture state.

Notably, in some instances, a posture state sensor may become disoriented after one or more posture state reference data has been defined. A posture state sensor may become disoriented, for example, when the physical location of the posture state sensor changes with respect to the patient's body. As an illustration, in cases in which the posture state sensor is implanted in a patient, the posture state sensor may physically move in position with respect to the patient, e.g., due to patient manipulation, long-term migration, acute patient movement, or other factors. As a result, due to the change in orientation, the posture sensor data generated by the posture state sensor for a given posture state may not match the posture state reference data that was previously acquired for the posture state. In such a case, the IMD may not accurately determine the posture state of a patient due to the movement of the posture state sensor.

In accordance with this present disclosure, in some examples, an IMD may be configured to reorient a posture state sensor, e.g., by redefining one or more sets of posture state reference data based on posture state sensor data obtained from the posture state sensor when the patient consciously resides in selected posture states. Notably, therapy information associated with the previously defined posture state reference data can be retained and associated with the newly defined posture state reference data, thereby avoiding the need to reacquire or reset the therapy information, which may be time consuming for the patient and/or clinician and result in loss of valuable information.

In some examples, the posture state reference data may define a reference coordinate vector that corresponds to a three-dimensional (x, y, z) set of coordinates obtained as posture sensor data for a given posture state, and a range of coordinates within a predetermined distance from the vector. The range may be expressed as tolerance angle, such that the vector and angle define, in effect a cone-like posture volume, i.e., a posture cone. Alternatively, the range may be expressed as a range of cosine values computed for the reference coordinate vector and vectors within the posture cone. As will be described, depending on the posture sensor reference data used to define the posture cone, a posture cone may be associated with a specific posture state of a patient. In any case, a posture cone formed by the posture state reference data may define a range of posture sensor data generated by the posture state sensor that indicates when a patient is occupying the posture state.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another. Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, pelvic pain, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms, e.g., pain or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
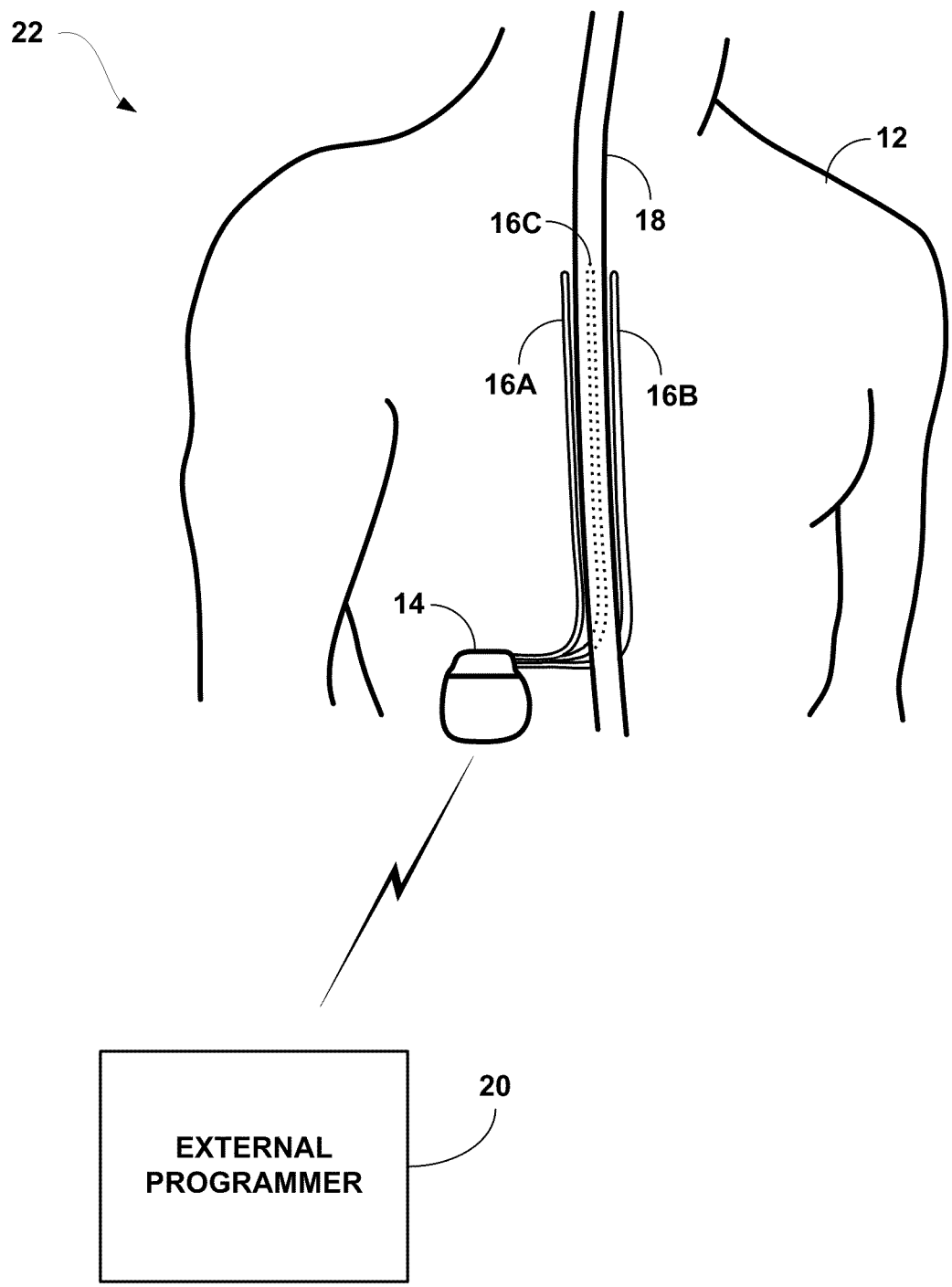
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
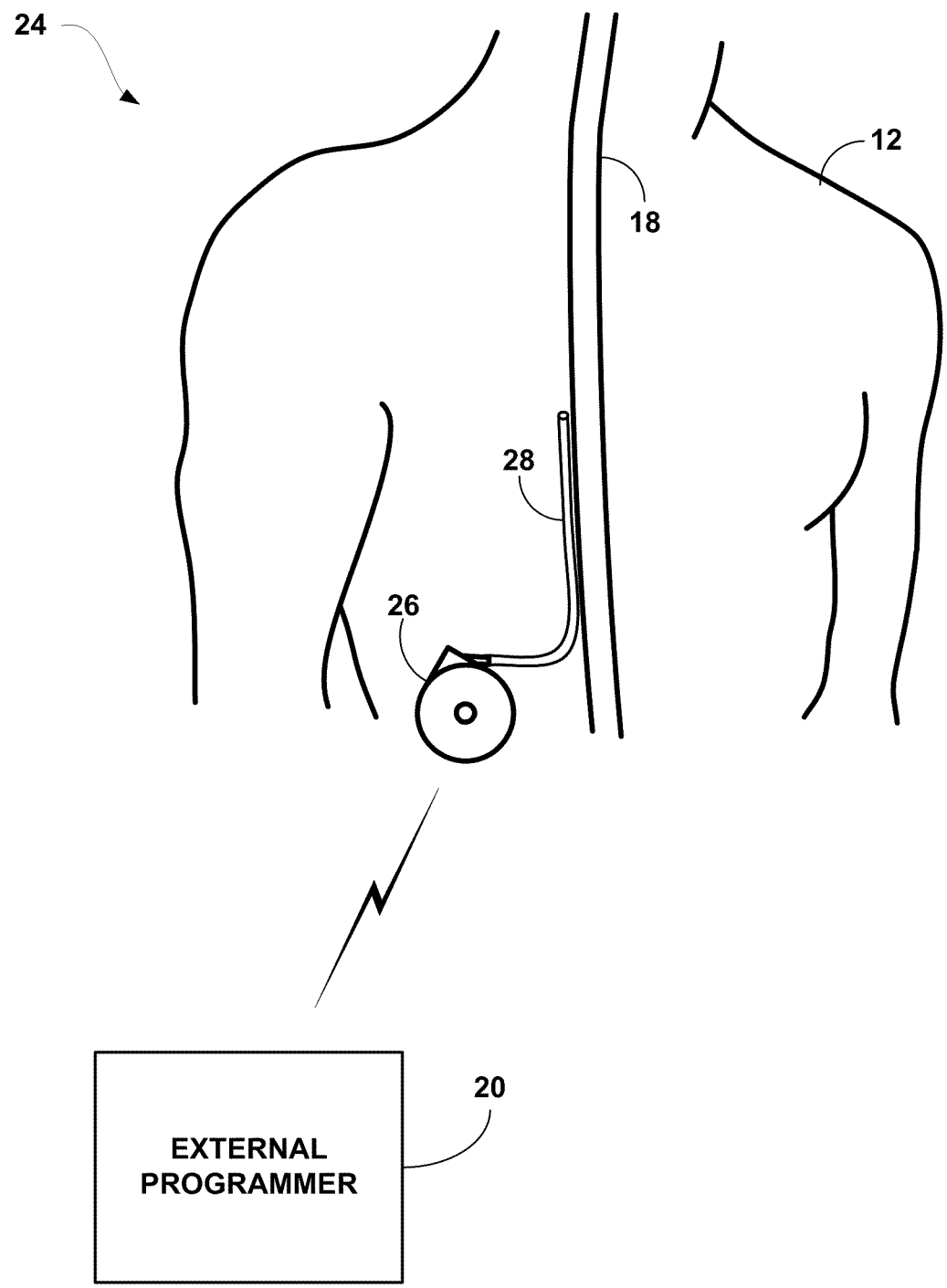
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 includes a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
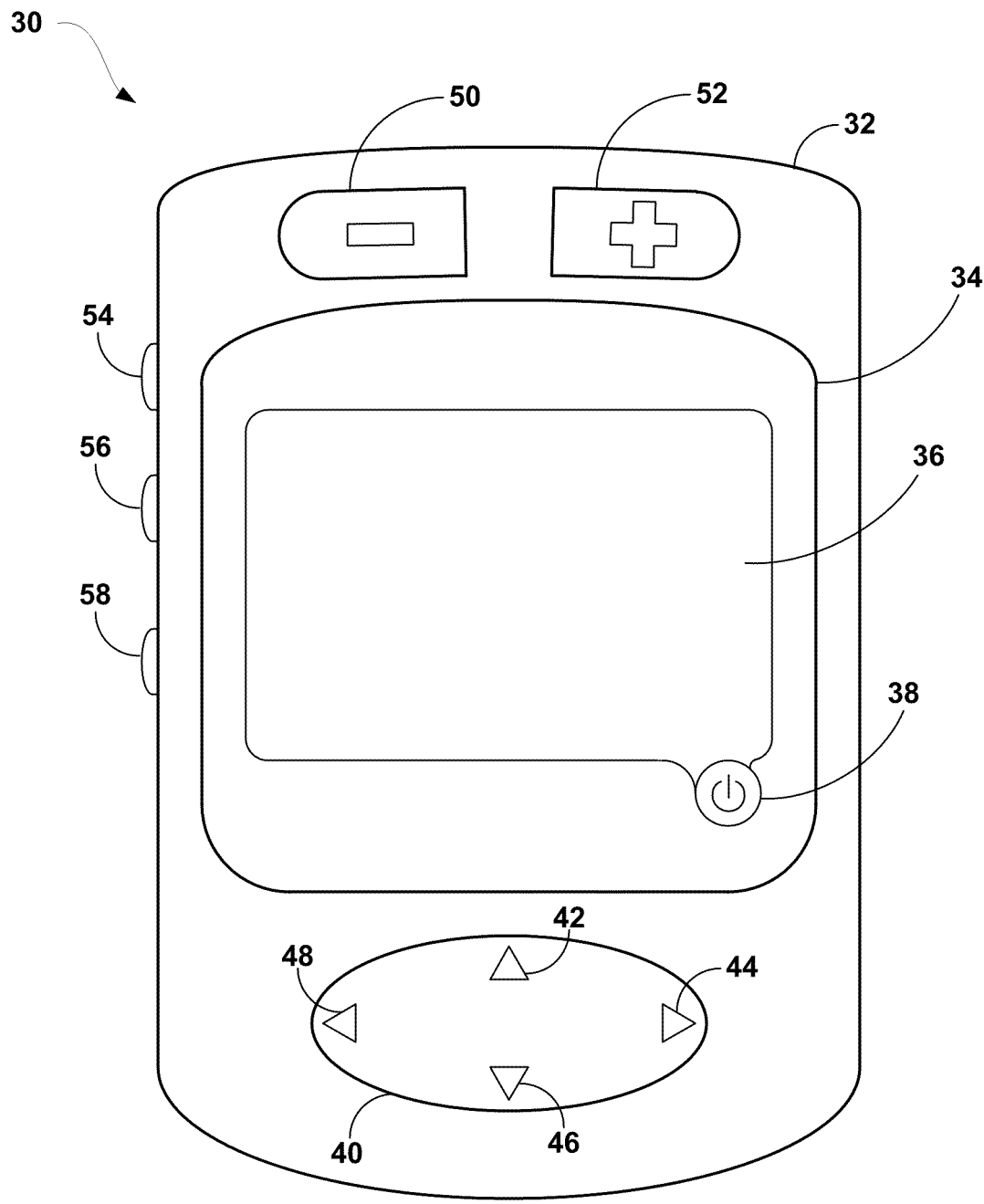
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any item highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either buttons 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
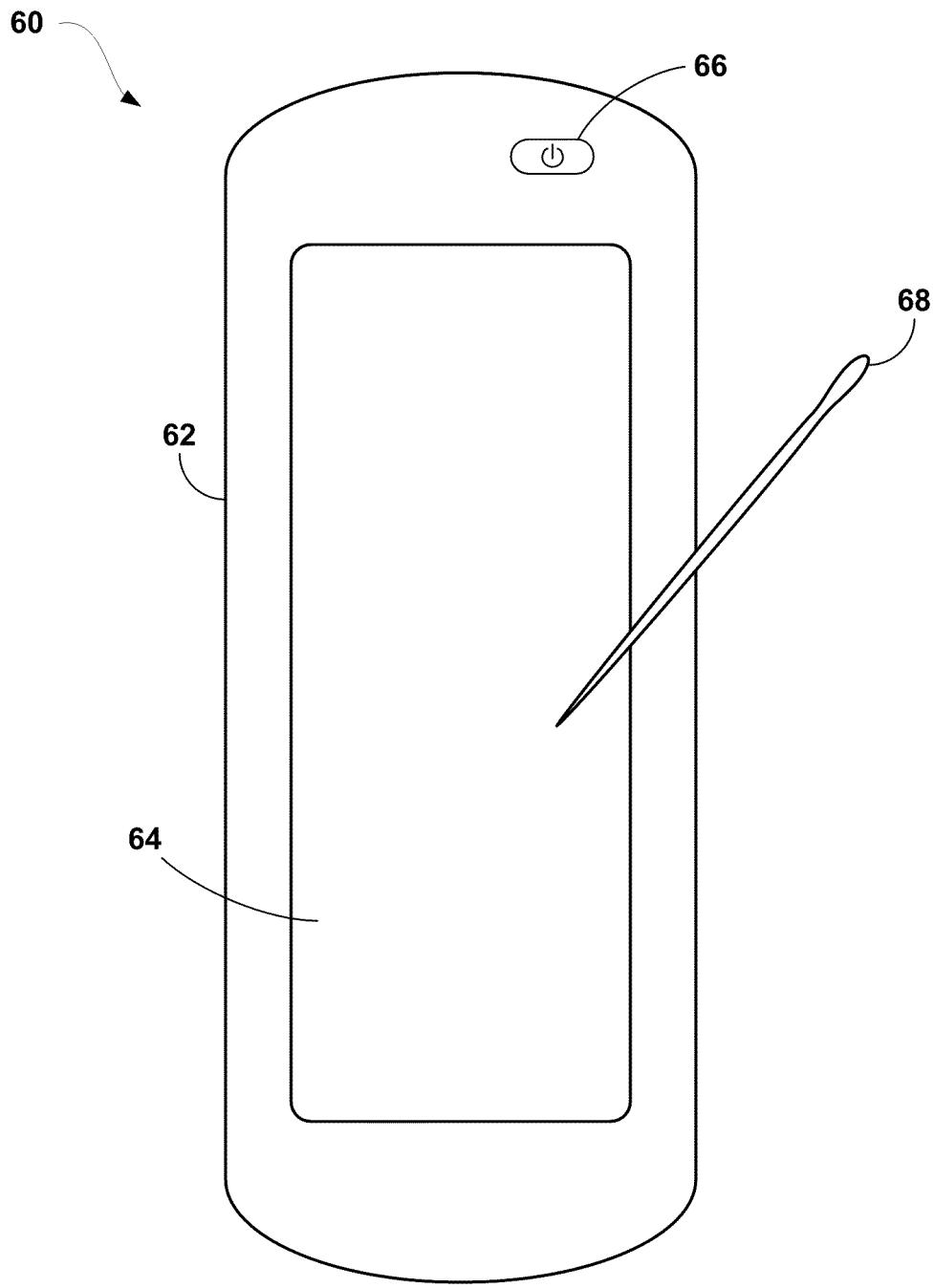
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameter values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
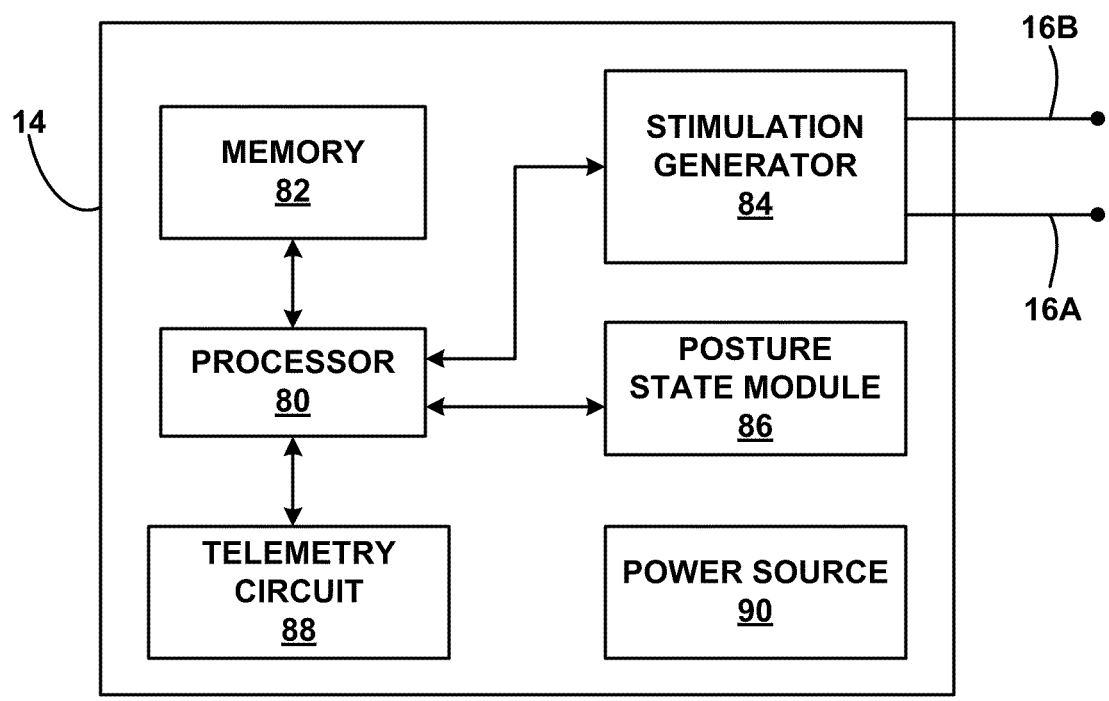
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and approximately 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes one or more accelerometers, such as three-axis accelerometers, capable of detecting static orientation or vectors in three-dimensions (e.g., x, y, z coordinate vectors). Example accelerometers may include a micro-electro-mechanical systems (MEMS)-based accelerometer. In other examples, posture state module 86 may alternatively or additionally include one or more gyroscopes, piezoelectric crystals, pressure transducers or other sensors to sense the posture state of patient 12. Posture sensor data generated by posture state module 86 and processor 80 may correspond to an activity and/or posture undertaken by patient 12 or a gross level of physical activity, e.g., activity counts based on footfalls or the like.

Posture sensor data from posture state module 86 may be stored in memory 82 for later review by a clinician, used to adjust therapy, present a posture state indication to patient 12 (e.g., via patient programmer 30) or some combination thereof. As an example, processor 80 may record the posture state parameter value, or output, of the 3-axis accelerometer as posture sensor data and use the posture sensor data to form posture state reference data for a certain predefined posture indicated by the posture sensor data. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed posture states. Therefore, IMD 14 may be configured to provide posture-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

Posture sensor data from posture state module 86 that indicates the posture state may constantly vary throughout the day of patient 12. However, a certain activity (e.g., walking, running, or biking) or a posture (e.g., standing, sitting, or lying down) may include multiple posture sensor data values from posture state module 86. Memory 82 may include definitions for each posture state of patient 12 based on posture state reference data. In one example, the definitions of each posture state may be illustrated as a cone in three-dimensional space. Whenever the posture sensor data, e.g., a coordinate vector, from the three-axis accelerometer of posture state module 86 resides within a predefined cone defined by the posture state reference data, processor 80 indicates that patient 12 is in the posture state of the cone. In other examples, posture sensor data from the 3-axis accelerometer may be compared to a look-up table or applied to an equation to determine the posture state in which patient 12 currently resides.

Posture-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient, assuming proper orientation of the sensor to the patient's body.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a coordinate vector and an associated tolerance, which may be a distance from the coordinate vector. Another example of an activity parameter value relates to acceleration. The value quantifying a level of change of motion over time in a particular direction may be associated with this parameter referenced in the activity parameter value.

IMD 14 wireless communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
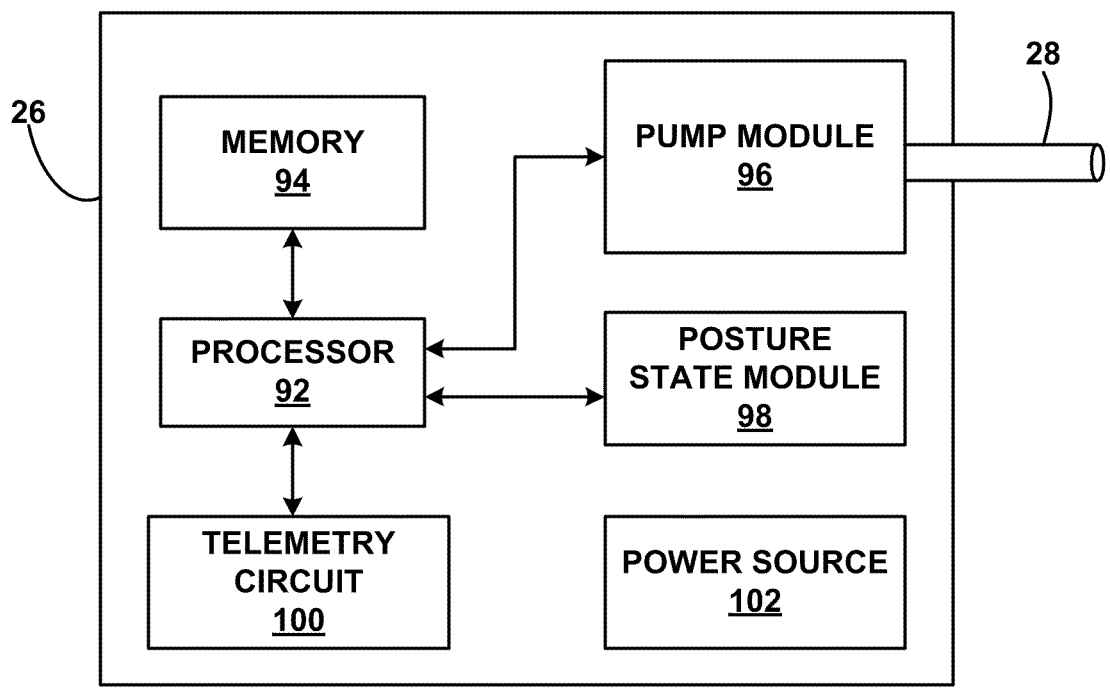
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12. Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture.

Figure 6:
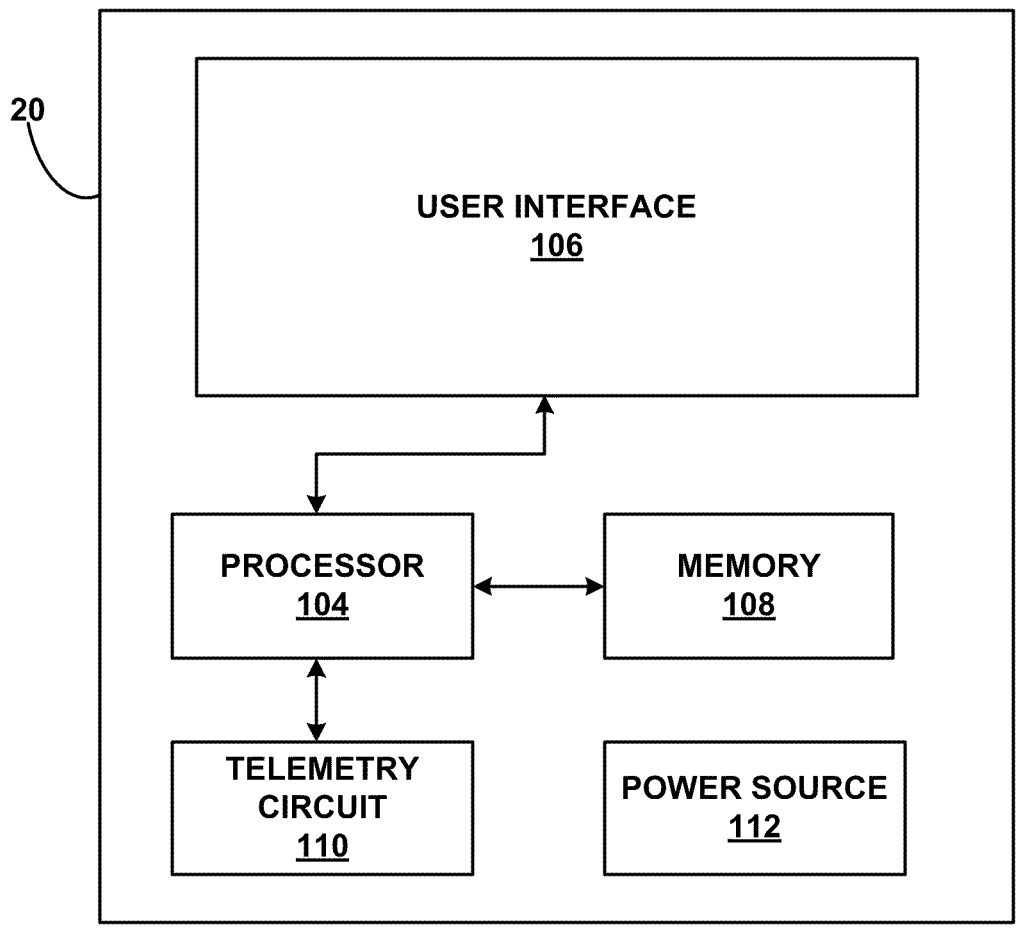
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture-responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12, or another user (e.g., a patient caretaker) interacts with user interface 106 in order to manually change the stimulation parameter values of a program, change programs within a group, turn posture-responsive stimulation ON or OFF, view therapy information, view posture state information, or otherwise communicate with IMDs 14 or 26.

User interface 106 may include a screen and one or more mechanisms, such as, buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
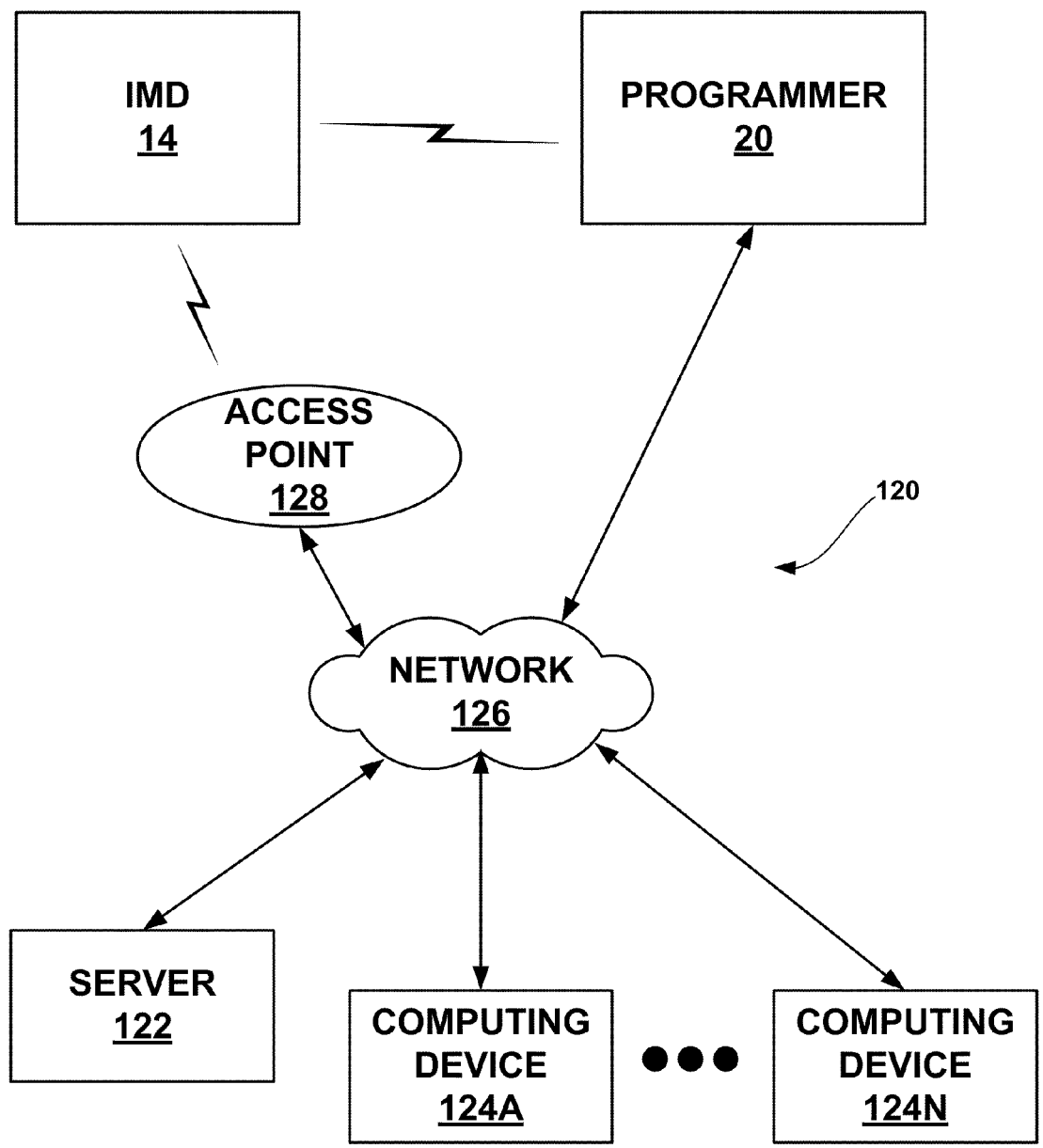
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

Using system 120 of FIG. 7, a clinician, physician, technician, or even patient 12, may review objectivity data with respect to the posture states of patient 12. The objectivity data may be sleep quality information or proportional posture information that indicates how patient 12 has been moving during the symptom diagnosis or delivered therapy. The user may remotely monitor the progress and trends of patient 12, limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
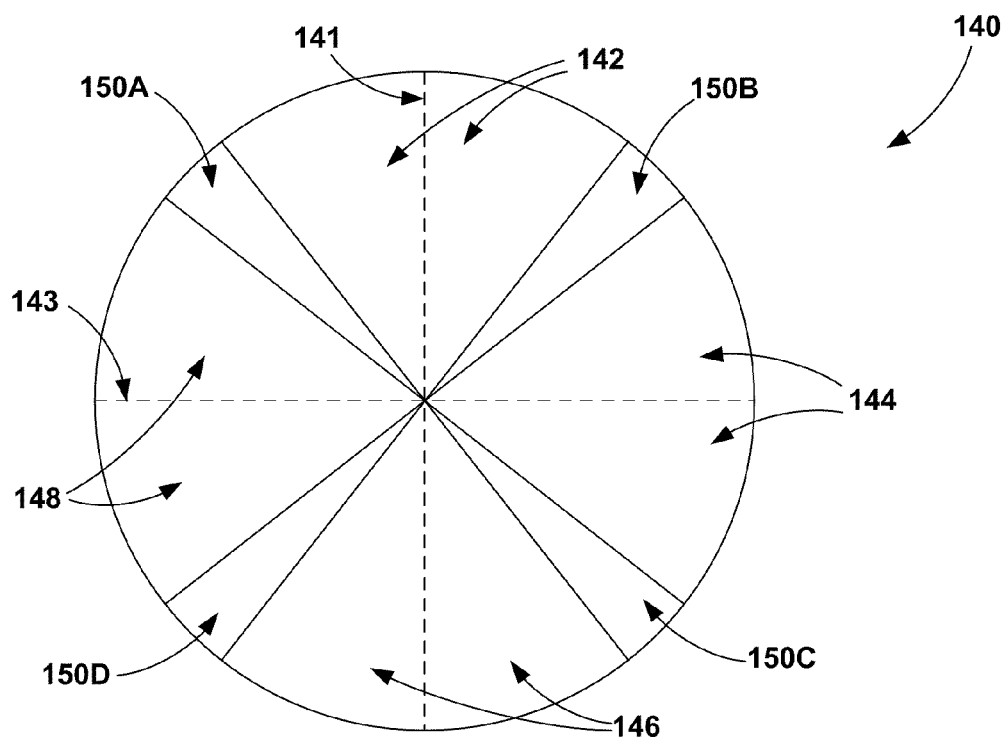
FIGS. 8A-8C are conceptual illustrations of example posture state spaces within which postures state reference data may define the posture state of a patient.
Figure 8B:
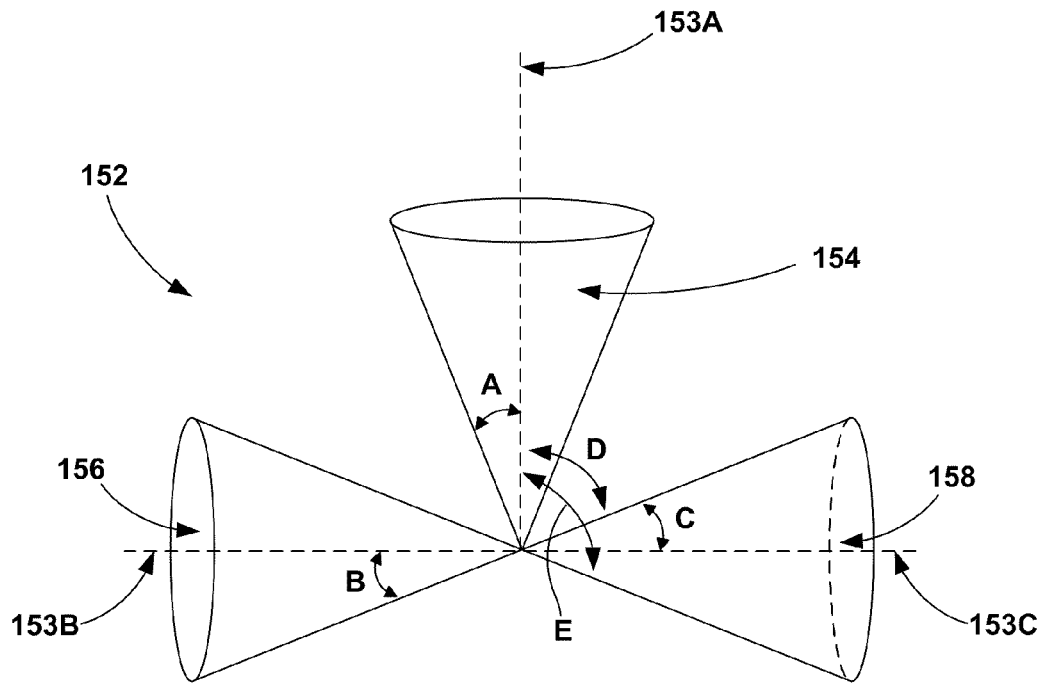
Figure 8C:
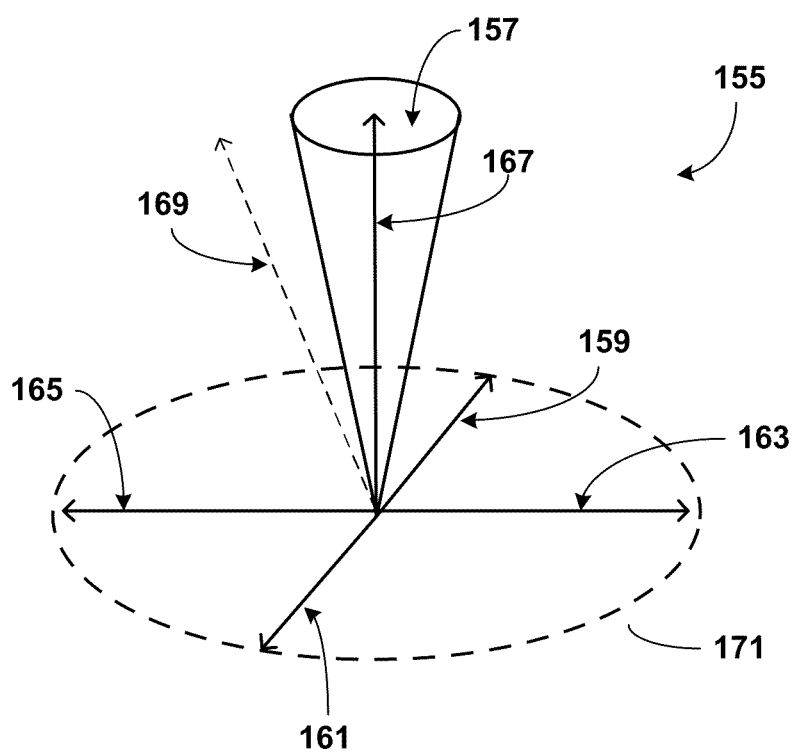

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate in which lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159 ×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
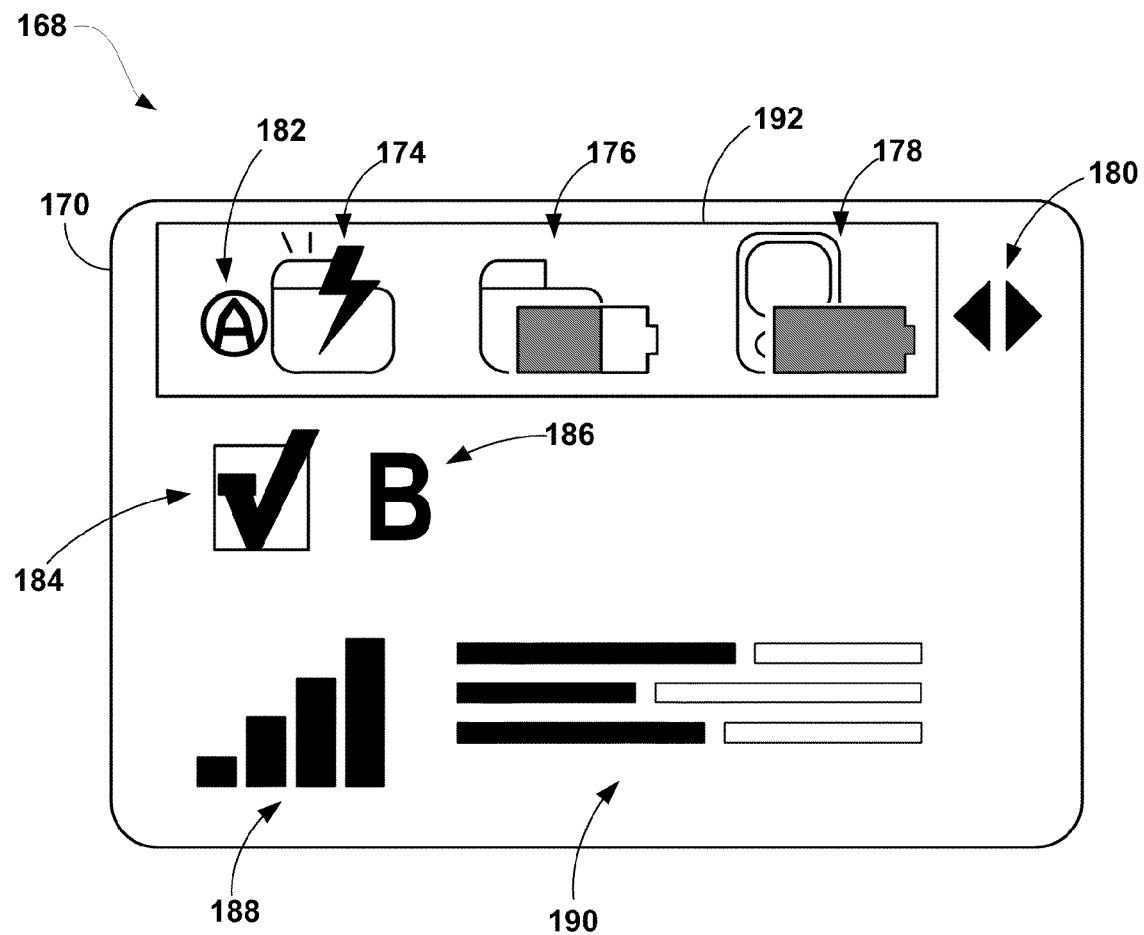
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 (FIG. 2) of control pad 40 of programmer 30 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the stored program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated, such that processor 80 automatically modifies therapy to patient 12 based upon the posture state detected by posture state module 86. In particular, automatic posture-responsive therapy may involve adjusting one or more therapy parameter values, selecting different programs or selecting different program groups based on the detected posture state of the patient. However, automatic posture response icon 182 is not present next to group identifier 186, indicating that group "B" does not have automatic posture-responsive therapy activated for any of the programs within group "B."

Some groups or individual programs in groups may support automatic posture responsive therapy. For example, automatic adjustment of one or more therapy parameter values in response to posture state indication may be selectively activated or deactivated based on settings entered by a clinician, or possibly patient 12. Hence, some programs or groups may be configured for use with posture-responsive therapy while other programs or groups may not be configured for use with posture-responsive therapy. In some cases, if posture-responsive therapy supported by the automatic posture response feature is desired, patient 12 may need to switch therapy to a different group that has automatic posture responsive therapy activated for IMD 14 to adjust therapy according to the patient 12 posture state.

Figure 10:
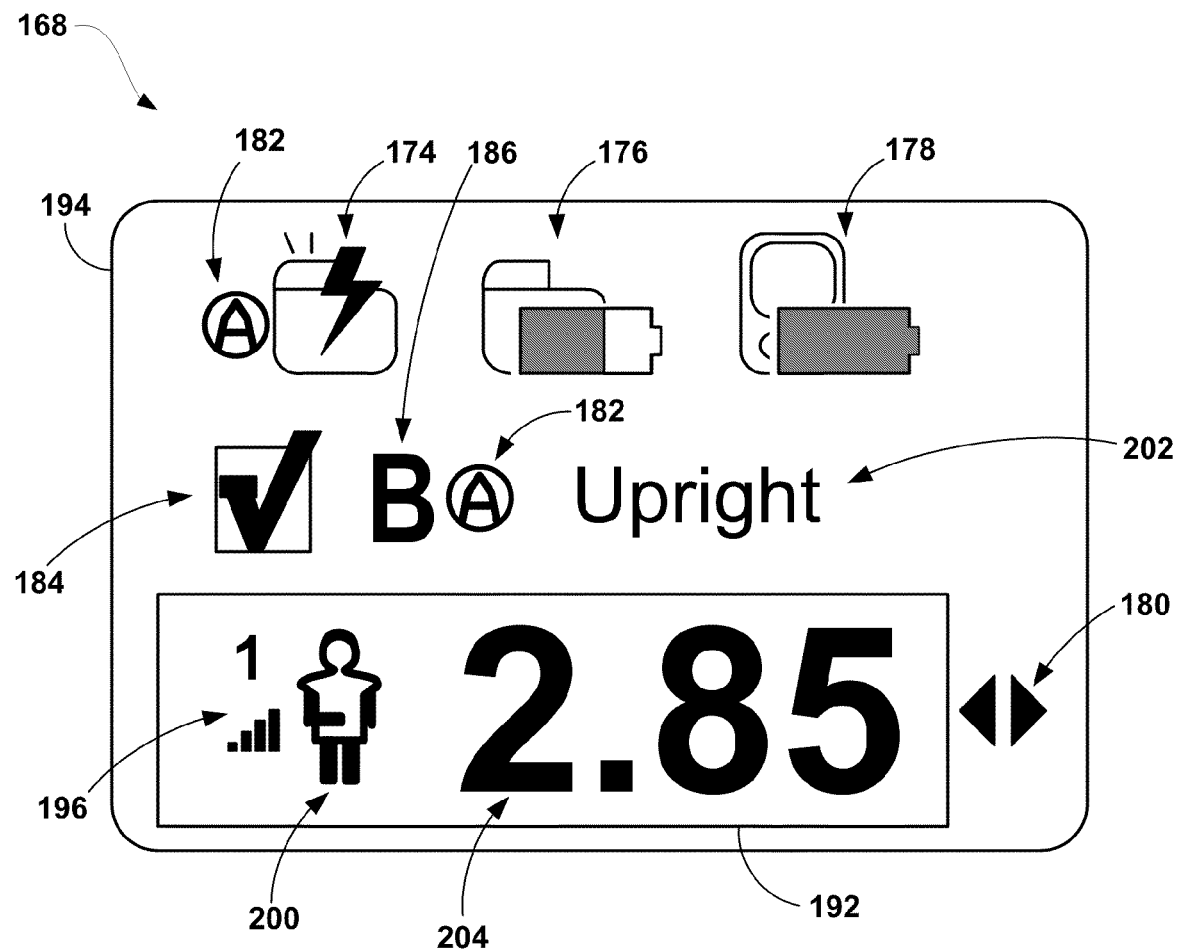
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or patient.

Group identifier 186 indicates that group "B" is active, and automatic posture response icon 182 indicates group "B" (containing one or more programs) is activated to allow IMD 14 to automatically adjust therapy according to the patient 12 posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture based on the output of posture state module 86 (FIG. 4). Supplementary posture state indication 202 supplements posture state indication 200 by explaining in words to patient 12 the exact posture being detected by posture state module 86 of IMD 14. Posture state indication 200 and supplementary posture state indication 202 presented via user interface 168 change according to the sensed, or detected, posture state detected by IMD 14. The posture state may be communicated to the external programmer immediately after IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 may view other programs within group "B" using selection arrows 180. Selection box 192 may be moved to select other screen levels with control pad 40 (FIG. 2) of patient programmer 30 in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

Figure 11A:
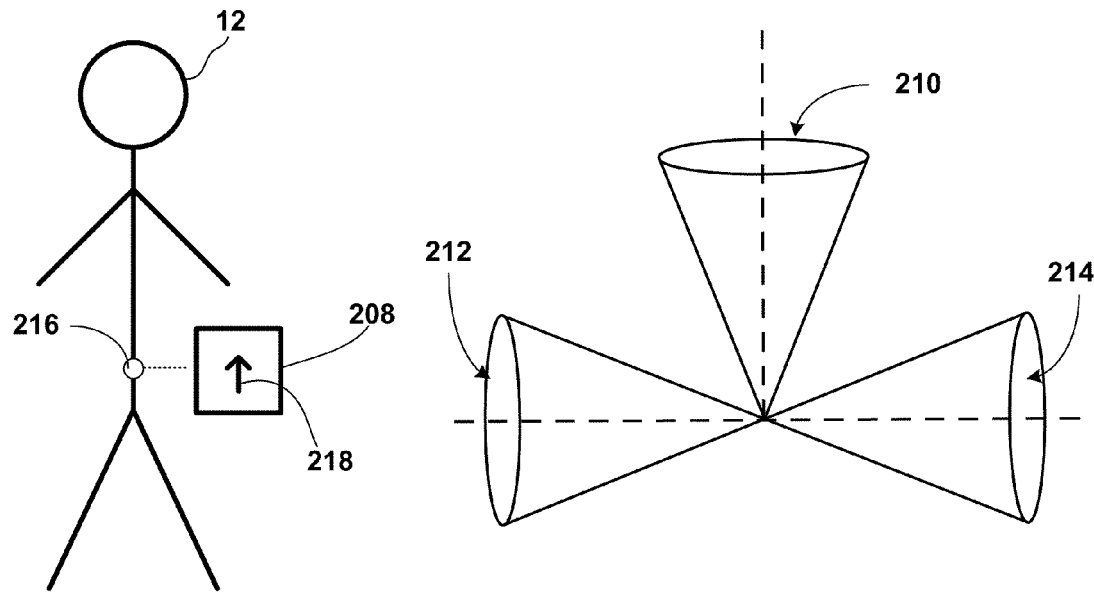
FIGS. 11A and 11B are conceptual illustrations of example posture cones used to define one or more posture states of a patient.
Figure 11B:
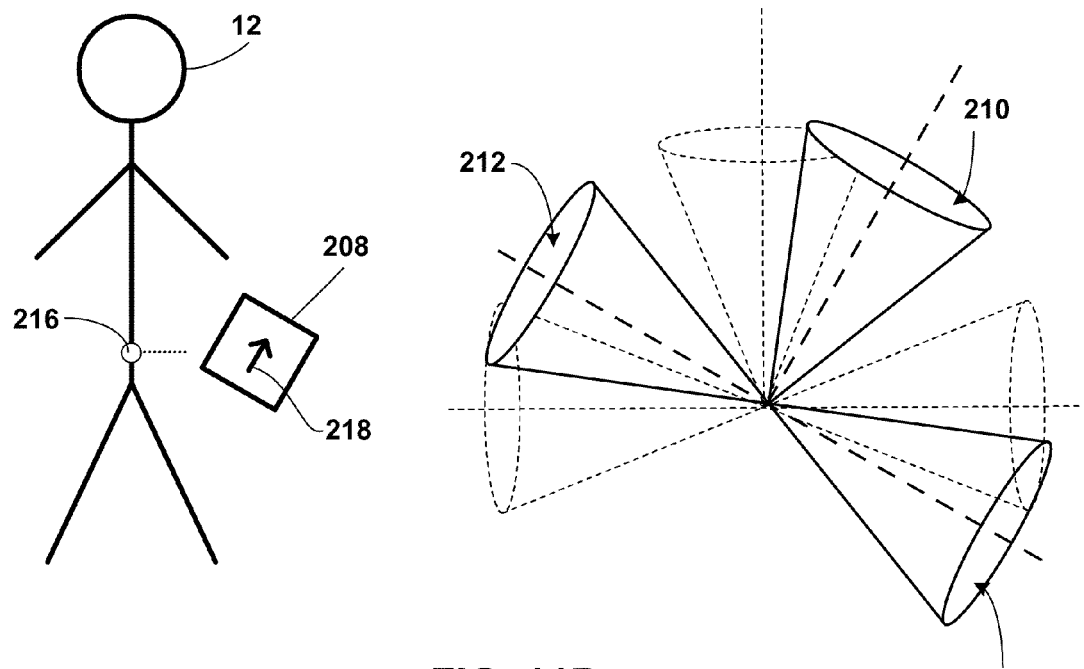

FIGS. 11A and 11B are conceptual illustrations of example posture cones used to define one or more posture states of patient 12 based on posture sensor data from sensor 208. As previously described, postures cones may represent a type of posture state reference data used by an IMD to detect the posture state occupied by a patient. Similar to posture cones 154, 156, and 158 of FIG. 8B, posture cones 210, 212, and 214 exist in a three-dimensional posture space to detect one or more posture states of patient 12 using one or more signals from sensor 12. In the example of FIG. 11A, posture cones 210, 212, and 214 indicate patient posture states of "upright," "lying right," and "lying left," respectively.

Sensor 208 may be part of a posture state module, such as posture state module 86 (FIG. 4) described above, included in IMD 216. IMD 216 may be implanted in patient 12 at the relative location indicated in FIGS. 11A and 11B. Sensor 208 may include a 3-axis accelerometer located within the housing of IMD 216, the signal of which may be analyzed by IMD 216 to detect the posture state of patient 12. For example, after being implanted, IMD 216 detects one or more posture states of patient by comparing the output signal of sensor 208 to posture state reference data defining posture cones 210, 212, and 214. IMD 216 may then modify stimulation therapy being delivered to patient 12 based on the posture state detected by IMD 216 using posture cones 210, 212, and 214. For ease of illustration, to show the physical orientation of sensor 208 with respect to patient 12 in FIGS. 11A and 11B, sensor 208 is shown outside of patient 216 and with reference arrow 218. However, sensor 208 ordinarily will be located within patient 12 or externally fixed to patient 12, and may form part of IMD 216 or part of a separate implanted and/or external device that communicates posture sensor data to IMD 216.

Postures cones 210, 212, and 214 may be defined based on one or more of the characteristics of posture sensor data produced by sensor 208 while patient 12 occupies each of the respective posture states indicated by posture cones 210, 212, and 214. The posture sensor data may include x, y, z coordinate values that can be compared to a range of x, y, z coordinate values within respective posture cones. For example, upright posture cone 210 may be defined based on one or more characteristics of the posture sensor data, which form posture state reference data, while patient 12 occupies an upright posture state. Each respective posture cone 210, 212, and 214 may be defined using such a process after IMD 216, including sensor 208, is implanted in patient 12 and/or attached externally to patient 12. In this manner, posture cones 210, 212, and 214 may be defined based on the characteristics of the posture sensor data for each respective posture state, as produced by sensor 208 as it is physically oriented in patient 12.

In the example illustrated in FIGS. 11A and 11B, posture cones 210, 212, and 214 are defined for patient 12 when sensor 208 is physically oriented as shown in FIG. 11A. FIG. 11A also illustrates the relative space occupied by each of postures cones 210, 212, and 214 in the three-dimensional posture space used to define the postures states of patient 12. As described above, posture cones 210, 212, 214 may be defined by posture state reference data that include a reference coordinate vector and a particular tolerance value (e.g., a tolerance angle or cosine value). Using posture cones 210, 212, and 214, IMD 216 detects the posture state of patient 12 based on the characteristics of the posture state sensor data that corresponds to the space defined by each posture cone 210, 212, and 214.

However, as previously mentioned, in some instances a posture state sensor, such as sensor 208, may become disoriented relative to the body of patient 12 after posture state reference data has been obtained to define respective posture cones. Disorientation of posture sensor 208 may occur in situations in which the physical orientation of the posture state sensor changes with respect to the patient. For example, the physical orientation of sensor 208 with respect to patient 12 shown in FIG. 11B is different than that of the physical orientation of sensor 208 with respect to patient 12 in FIG. 11A. In particular, although patient 12 occupies substantially the same posture in FIGS. 11A and 11B, arrow 218 indicates that sensor 218 has changed physical positions from FIG. 11A to FIG. 11B, e.g., by rotating towards the patient's left side.

As a result of the movement of sensor 208 within patient 12, posture cones 210, 212, and 214 effectively change orientation in the three-dimensional posture space and are no longer accurate for patient 12. For example, as indicated by FIG. 11B, even though patient 12 occupies approximately the same posture as in FIG. 11A, the positions of posture cones 210, 212, and 214 in the posture space are different than those of the posture cones 210, 212, and 214 shown in FIG. 11A (shown as dashed lines in FIG. 11B). In such cases, the existing posture state reference data obtained during initial orientation may no longer be valid as a result of the later movement of posture sensor 208 relative to the body of patient 12.

Accordingly, using posture cones 210, 212, and 214, which are defined based on the characteristics of posture sensor data generated by sensor 208 when physically oriented as indicated in FIG. 11A, to detect the posture state of a patient based on the characteristics of the posture sensor data generated by sensor 208 when physically oriented as indicated in FIG. 11B may cause IMD 218 to incorrectly detect the actual posture states occupied by patient 12. In some examples, based on posture cones 210, 212, and 214 and posture sensor data from sensor 208 when physically oriented as indicated in FIG. 11B, IMD 218 may erroneously detect that patient 12 is not occupying a posture state that is defined by a posture cone even though patient 12 is actually in the posture state used to define the posture cone originally. Furthermore, depending on the extent of sensor movement, IMD may even detect that a patient is in one posture state, when in fact the patient is in a different posture state.

Consequently, IMD 218 may incorrectly determine the actual posture state occupied by patient 12 using posture cones 210, 212, and 214, after sensor 208 has changed from the position indicated in FIG. 11A to the position indicated in FIG. 11B. If IMD 218 delivers stimulation therapy based on the posture state detected using sensor 208, then IMD 218 may fail to deliver stimulation therapy when patient actually occupies the posture state programmed for delivery, or even deliver stimulation therapy configured to be delivered when patient 12 is in a posture state other than the posture state actually occupied by patient 12. In either case, the operation of posture responsive therapy may not work as effectively as desired.

While the example of FIGS. 11A and 11B are described with respect to posture cones 210, 212, 214 used to define the posture state of sensor, the disorientation of sensor 208, e.g., by shifting of sensor 208 within patient 12, may cause the same or similar problems in examples in which the posture state of patient 12 is determined using posture reference data defined by posture sensor output in general. For example, posture state sensor 86 may incorrectly determine the posture state of patient 12 defined using one or more posture reference vectors, such as lying reference vectors 159, 161, 163, 165 of FIG. 8C, when a posture sensor, such as sensor 208, is disoriented from the physical position of the sensor when the reference vectors where originally defined. Accordingly, examples are not limited to those in which a posture state module determines the posture state of a patient using one or more posture cones.

Figure 12:
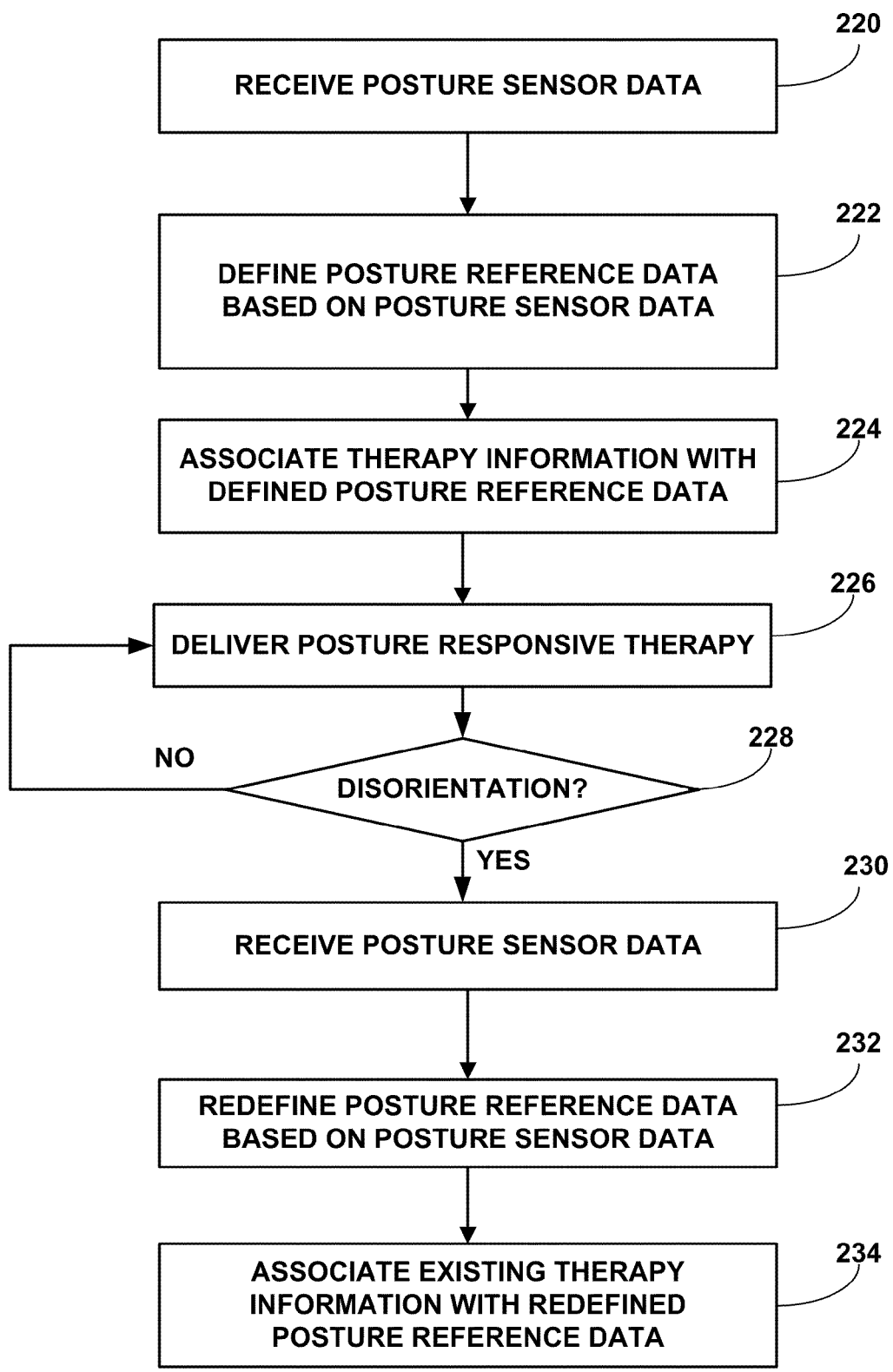
FIG. 12 is a flowchart illustrating an example technique for redefining one or more posture cones of a patient.

FIG. 12 is a flowchart illustrating an example technique for redefining one or more posture cones of a patient, e.g., to reorient posture sensor 208 to the body of patient 12 following disorientation as described with regard to FIG. 11. A user, such as patient 12 or a clinician, may initiate reorientation when it is believed that a sensor used to detect the posture state of patient 12 has become disoriented, i.e., shifted in position from an initial or previous orientation. For example, patient 12 or the clinician may notice that a posture display icon on display on the user interface display of a programmer or clinician programmer, e.g., user interface 106 of programmer 20 (FIG. 6), does not accurately represent an actual posture state of the patient. Alternatively, patient 12 or the clinician may note that posture-responsive therapy is not working in an expected manner, and may investigate the cause of the irregularity. As a further alternative, an IMD or programmer may be configured to automatically detect disorientation of the sensor.

Although the example technique of FIG. 12 is described with respect to posture cones, the same or similar technique may be applied with respect to redefinition of posture state reference data in general, whether arranged to define posture cones or other posture volumes, spatial ranges, or the like. Furthermore, for purposes of illustration, the technique of FIG. 12 is described with respect to IMD 14 implanted in patient 12, and in the case that IMD 14 is configured to deliver posture-responsive electrical stimulation therapy to patient 12. However, it is recognized that the example technique may apply to other devices and/or systems configured to detect a posture state of a patient and deliver posture-responsive therapy. For example, such a technique may be incorporated into drug therapy systems, including, e.g., IMD 26 for delivering drug therapy to patient 12.

As previously described, IMD 14 may be implanted in patient 12, and configured to deliver stimulation therapy to patient 12 based on the posture state occupied by patient 12. For example, posture state module 86 of IMD 14 detects the posture state of patient via posture state module 86 using one or more posture cones, as described herein. Posture state module 86 may contain a posture state sensor, such as a three-axis accelerometer. The posture sensor data produced by the posture state sensor may be analyzed with respect to one or more posture cones by posture state sensor 86 to detect the posture state of patient 12.

Initially, IMD 14, including the posture state sensor, may be implanted in patient 12 such that the posture state sensor occupies a relatively stable physical orientation with respect to patient 12. Once the posture state sensor and IMD 14 are implanted in patient 12, posture state module 86 may define posture state reference data for a particular posture state of patient 12 based on posture sensor data (222) received from the posture state sensor when patient 12 occupies the corresponding physical posture state (220). Examples of suitable techniques for defining posture state reference data include those described in co-pending U.S. Provisional Patent Application No. 61/080,049, to Eric Panken, filed Jul. 11, 2008, titled "POSTURE STATE DETECTION SYSTEM AND METHOD," the entire content of which is incorporated herein by reference, and co-pending U.S. Patent Applications to Eric Panken, filed on the same date as the present application, titled "POSTURE STATE Classification for a Medical Device", the entire content of which is incorporated herein by reference.

In some examples, posture state module 86 defines a posture state cone based on the posture state reference data, which may include a posture reference coordinate vector derived from the posture state sensor data received at a time when patient 12 is actually occupying a known posture state. In addition, as described above, in some examples, a tolerance may also be defined as part of the posture state reference data. The tolerance may, in effect, define the maximum distance that posture coordinates may be from the posture reference coordinate vector while still being considered in the same posture state defined by the posture reference coordinate vector. For example, with respect to cone 156 of FIG. 8B, the value of angle B may be correspond to the tolerance of posture cone 156 with respect to a reference vector aligned with axis 153B. As another example, a cosine value may define the tolerance relative to the reference vector, in a manner the same or similar to that described above.

In such cases, once a posture state is defined by a posture cone, posture state module 86 may receive posture sensor data from the posture state sensor and determine a sensed vector based on the posture state sensor data. If the determined sensed vector is within the maximum distance from the posture reference vector of the defined posture cone, e.g., as determined by the tolerance, posture state module 86 classified patient 12 as being in the posture state represented by the posture cone.

The process of defining posture state reference data based on received posture sensor data may be repeated to define multiple posture cones defining multiple posture states of patient 12, e.g., posture states of patient 12 that may be useful with respect to the delivery of electrical stimulation therapy. In this manner, one or more posture state cones may be defined such that posture state module 86 can detect when patient 12 occupies a posture state defined by one of the posture cones based on the posture sensor data. As previously described, IMD 14 may be configured to deliver electrical stimulation therapy based on the posture state occupied by patient 12. For example, based on the posture state of patient 12 detected by posture state module 86 of IMD 14, stimulation generator 84 may generate and deliver therapy according to one or more stimulation programs that are defined to provide effective therapy to patient 12 when patient occupies the posture state detected by IMD 14. When posture state module 86 determines that patient 12 changes posture states based on the posture state sensor data and defined posture cones, IMD 14 may modify one or more therapy parameter values, of the stimulation therapy, such as current or voltage amplitude values, according to the stimulation program that is associated with the new posture state occupied by patient 12.

In some examples, IMD 14 may associate therapy information with posture state reference data for a defined posture cone (224). For example, processor 80 or posture state module 86 may store a look-up table or other data structure that contains records in memory 82, in which each record contains therapy information previously associated with a defined posture state. In some examples, the therapy information includes stimulation programs corresponding to particular posture states of patient 12. These programs may define stimulation parameter values that previously provided effective stimulation therapy to a patient when they were in a respective posture state indicated by posture state reference data.

Therapy information may include any of a variety of information useful in controlling posture-responsive therapy, analyzing posture-responsive therapy, analyzing patient posture state activity, patient therapy adjustments, or the like. For example, therapy information may include information indicating a history of patient posture state activity over a period of time, such as statistics relating to the number of time patient 12 has assumed a posture state, the number of times that patient 12 has undertaken a particular posture state transitions from one posture state to another, the amount of time that patient 12 has spent in respective posture states, particular times of the day associated with different posture states, and related statistical information such as average, mean, trend information, and the like. In some respects, this type of information may be generally referred to as therapy objectification information in the sense that it may be used by a clinician to objectively indicate posture, activity level, and therapeutic efficacy for patient 12. In turn, such objectification information may aid the clinician in further programming of IMD 14 to enhance performance and efficacy. Objectification information, in some implementations, may be obtained as part of an "objectification" mode of IMD 14, in which IMD 14 collects and stores such information for review by a clinician or for use in automated therapy or guided programming of therapy.

Therapy information also may include stimulation therapy parameter values for each posture state such as voltage or current amplitude values, pulse width values, pulse rates, electrode configurations, program groups and programs used for particular posture states. In addition, therapy information may include information indicating a history of patient therapy adjustments in different postures states, including parameter value increases, decreases and other adjustments, and related statistical information such as parameter average, mean, trend information, and the like. In some respects, this type of information may generally be referred to as parameter information in the sense that it may be used to identify and program efficacious parameters for different posture states.

While therapy information may be useful in programming IMD 14, therapy information also may be useful in evaluating therapeutic efficacy, patient activity levels, patient quality of life, or other therapy-related metrics. In some cases, parameter information may be collected and stored by IMD 14 as part of a "record" mode. Hence, in some implementations, IMD 14 may have one or more of objectification, record, and posture responsive therapy modes, where the objectification and record modes may be useful in programming parameters for use in the posture-responsive therapy mode.

As another example, when initially defining a posture cone based on posture state reference data, IMD 14 may store the posture cone definition information as an entry in a look-up table or other data structure. One or more stimulation programs that may provide effective stimulation therapy to patient 12 when occupying the posture state may be stored in the table to correspond to the defined posture cone. When IMD 14 receives posture state sensor data, it may compare the data to all of the defined posture cones stored in the look-up table until a match is found. If the posture state sensor data falls within a posture cone defined by the posture state reference data, IMD 14 then may control the stimulation according to the stimulation program(s) corresponding to the posture cone in the look-up table. Additionally, any subsequent modifications to the stimulation programs may also be stored in such a look-up table.

In some examples, the therapy information associated with a defined posture cone may include modifications to the definition of the posture cone itself. Posture cone modifications may include adjustments to the tolerance value used in conjunction with a posture reference vector, as described above. While the initial tolerance value may be predefined value, such as an angle or cosine value, it may be observed that the resulting posture cone may define a space that is too small or too great based on the therapy experienced by patient 12 over time. Accordingly, a new tolerance value may be defined for a posture cone. This tolerance value adjustment may also be stored as an entry in a look-up table such that the value adjustment is associated with the respective posture cone definition it is modifying.

Therapy information can be valuable to the patient and/or clinician provided that it is properly associated with posture state reference data that accurately defines the posture states. When the accuracy of previously obtained posture state reference data is compromised due to disorientation of the posture state sensor (e.g., as described with respect to FIGS. 11A and 11B), the therapy information associated with the posture state reference data is less useful. However, acquisition of the therapy information may be a labor- and time-intensive effort. In some cases, the therapy information may have been obtained over the course of several days, weeks or months, and required substantial time and effort by patient 12 and/or clinician. Therefore, reacquisition or resetting of the therapy information is generally undesirable.

In accordance with various aspects of this disclosure, therapy information obtained for patient 12 may be retained and associated with posture state reference data that is newly defined as a result of a reorientation procedure. The therapy information, or at least the therapy information gathered prior to the disorientation of a posture state sensor, is still relevant for the actual posture states of the patient. When disorientation occurs, however, the previously obtained posture state reference data no longer accurately defines the posture states of patient 12. Upon reorientation, the newly defined posture state reference data accurately defines the posture states of patient 12. Therefore, the previously obtained therapy information can be associated with the newly defined posture state reference data for the appropriate posture states, rather than discarded.

As an illustration, assume that the therapy information includes, among other things, amplitude values that define the different stimulation amplitude values that are delivered for programs in a program group when the patient occupies different posture states. For example, the stimulation amplitude values may have been selected and defined as a result of a fundamental recording mode in which manual patient adjustments were monitored over a period of time to obtain an indication of efficacious amplitude values useful in different posture states, further manual adjustments made by the patient following activation of posture responsive therapy, and in-clinic evaluation of the patient by the clinician. In such a case, it is undesirable to simply discard such amplitude values when a posture state sensor becomes disoriented with respect to patient 12. Rather, because the amplitude values relate to posture states, and posture states reside at a level of abstraction above the actual posture state reference data used to define the posture states, the amplitude values can simply be associated with posture state reference data that is newly defined for the pertinent postures as a result of a reorientation process. In this manner, the relationship between the amplitude values and the posture states to which they pertain can remain intact following reorientation.

With further reference to FIG. 12, as previously described, at some point in time, including a point in time after therapy information has been associated with a posture cone, the posture state sensor implanted in patient 12 may become disoriented, e.g., as a result of a physical shifting of a posture state sensor relative to patient 12. As a result, the ability of IMD 14 to accurately detect the posture state actually occupied by patient 12 using the defined posture cones may become impaired, as illustrated, e.g., by FIGS. 11A and 11B.

In some examples, processor 80 of IMD 14 may monitor the status of a posture state sensor to determine if it has become disoriented. For example, processor 80 may be configured to utilize typical patient posture state behavior over a period of time, e.g., daily, weekly, etc., to determine if it is likely that the posture state sensor has been disoriented. For example, processor 80 may be configured to recognize typical periods of time that patient 12 is sleeping and, thus, should be occupying one or more lying down posture states. In such cases, if IMD 14 determines that the detected posture state of patient 12 at those times is not a lying posture state, then processor 80 may take suitable action, such as alerting patient 12 or a clinician via programmer 30 (FIG. 2) that the posture state sensor may have become disoriented and that one or more posture states may need to be redefined.

In some examples, if processor 80 determines that the posture state sensor may have been disoriented, IMD 14 may suspend the automatic delivery of electrical stimulation according to the posture state detected using the posture state sensor. In such cases, IMD 14 may suspend all delivery of electrical stimulation therapy or, alternatively, it may provide electrical stimulation according to a stimulation program that is determined to be "safe" to be delivered to patient in any posture state, although the effectiveness of the therapy may be less than optimal. As a further alternative, IMD 14 may suspend posture-responsive therapy and revert to a therapy mode that is not posture responsive.

As another example, processor 80 may monitor patient posture state to determine one or more patterns of patient behavior or activity over time. If processor 80 detects a posture state or a series of posture states that are not consistent with the determined pattern, then IMD 14 may again take an appropriate action such as that described above. As another example, processor 80 may monitor for sensor disorientation using input from patient 12. Patient 12 may communicate with processor 80 periodically to identify a posture state that they actually occupy or are about to actually occupy. Processor 80 may verify that the posture state detected via posture state module 86 using the defined posture cones is consistent with the posture state that the patient indicated. Such as technique may be used, e.g., when patient 12 is about to lie down to sleep.

More generally, in such examples, patient 12 may indicate to patient programmer 30 the actual posture state that they are occupying. Programmer 30 may then interrogate IMD 14 to determine what posture state that posture state module 86 is detecting that patient 12 is occupying based on the defined posture cones. If the posture state detected by posture state module 86 is different that the posture state communicated by patient 12 to programmer, programmer 30 may indicate a potential disorientation of the posture state sensor used by posture state module 86 to detect the patient's posture state. In some cases, programmer 30 may suspend the therapy being delivered to patient 12 and/or require patient 12 to redefine one or more posture states. As a further alternative for determining that a posture state sensor has become disoriented, as mentioned above, patient 12 or clinician may simply observe a mismatch between a posture display icon or text, e.g., as communicated via programmer 30 or 60, and an actual posture state occupied by patient 12.

Upon detection or indication of disorientation (228), a patient or clinician may interact with a user interface of a patient programmer and/or clinician programmer to initiate a posture state sensor reorientation procedure. Conversely, if no sensor disorientation is detected, IMD 14 may continue to deliver posture-responsive therapy (226) to patient 12. However, if disorientation is detected (228), IMD 14 may suspend posture-responsive therapy pending successful reorientation of the posture state sensor. In a reorientation procedure, posture state reference data used to define existing posture cones may be redefined based on the posture state sensor data produced by the posture state sensor and received by processor 80 for different posture states with the posture state sensor in its current orientation (230).

To redefine the posture state reference data that defines a posture cone or posture reference coordinate vector, substantially the same process used to initially define the posture cones may be used. For example, a posture reference vector may again be defined based on the posture state sensor data generated by the posture state sensor when a patient actually occupies a posture state, and in the case of a posture cone, a tolerance value, e.g., angle or cosine value, may be used to define the posture cone. In particular, IMD 14 or a programmer may redefine the posture state reference data based on the posture sensor data generated by the posture state sensor (232). Posture state module 86 of IMD 14 may then use the redefined posture state reference data to detect the posture state of patient 12 based on subsequently received posture sensor data. In this manner, IMD 14 may again be able to correctly determine the posture state actually occupied by patient 12 despite the fact that the posture state sensor had become disoriented from its initial orientation, e.g., as a result of the posture state sensor changing physical orientation with respect to patient 12.

As previously described, in some examples, existing therapy information that was previously obtained when the posture state sensor was in its initial orientation may be associated with the redefined posture state reference data (234), thereby maintaining the relationship between the therapy information and the actual posture states occupied by the patient. The therapy information may be associated with the redefined posture state reference data in memory 82 of IMD 14 and/or memory of an external programmer, so that the therapy information may be used in the posture-responsive therapy, e.g., to deliver appropriate stimulation parameters for different posture states, and/or in other operations such as analysis and review of posture state activity, posture state transitions, patient therapy adjustments, and the like.

Again, rather than erase the therapy information associated with a posture cone defined by posture state reference data defined before the posture state sensor was disoriented, in some examples, IMD 14 may automatically associate the therapy information with the new posture cone (defined by the redefined posture state reference data) that is replacing the old posture cone (defined by the previously defined posture state reference data). In this manner, the process of associating the therapy information with the new posture cone does not have to be repeated as when the initial posture cone was defined. Further, any therapy modifications that have been made to one or more stimulation programs associated with an old posture cone may automatically be associated with the new posture cone defining the same or similar posture state of patient 12.

For example, processor 80 of IMD 14 may store the new posture cone information in memory 82 as a new entry in a look-up table or other data structure, or replace part of a look-up table mapping with the newly defined posture state reference data. Although, in some examples, the old posture cone definition information may be erased and replaced by the new posture cone definition information (i.e., the redefined posture state reference data), in other examples, the new posture cone definition information may be entered without erasing the old posture cone definition information. Instead, IMD 14 may "deactivate" the old posture cone definition information and "activate" the redefined posture state reference data defining the new, reoriented posture cones. Subsequently, when IMD 14 is determining whether or not posture state sensor data corresponds to a posture cone definition stored in the look-up table, it may only compare the signal to the active posture state reference data for each respective posture cone. However, all of the therapy information that was associated with the now inactive posture state reference data for the previous posture cones may be automatically associated with the newly active posture state reference data for the newly reoriented posture cones in the look-up table.

As previously mentioned, therapy information associated with a defined posture cone may include modifications to the definition of the posture cone itself. In some examples, these modifications may be automatically associated with the redefined posture cone for the respective posture state. For example, the modification, e.g., an adjusted tolerance value, such as a tolerance angle or cosine value, may be automatically applied to the posture cone definition information stored in a look-up table. In this manner, therapy information used to tailor posture cone definitions may automatically applied to the new posture cone without requiring patient 12, with or without the assistance of a clinician.

In some examples, posture reference data may be redefined by redefining a posture reference vector and also a new tolerance value, e.g., a tolerance angle or cosine value. If one or more adjustments had been made to the tolerance value used with the previously defined posture reference vector, then a similar adjustment may be made to the new tolerance value based on stored therapy information relating to the tolerance value adjustments. In other examples, posture reference data may be redefined by redefining a posture reference vector but not a new tolerance value. In such an example, the tolerance value used with the previously defined posture reference vector may be stored as therapy information and then used with the redefined posture reference vector.

In some cases, the therapy information may not be automatically associated with posture state reference data for a redefined posture cone, but instead patient 12 or a clinician may be given the option of associating parts or all of the therapy information from the old posture cone to the new posture cone, for example, via programmer 30 (FIG. 2). The ability to selectively associate all or part of the previously obtained therapy information with the redefined posture state reference data may provide patient 12 or a clinician with added flexibility, particularly in the event that patient 12 or the clinician would like to reacquire new therapy information for all or selected items of therapy information upon reorientation.

Furthermore, in some examples, the posture state detected by IMD 14 may be objectified to evaluate one on more aspects that may be based on the posture state of a patient, as mentioned above. By importing the modification made to a previous posture cone, a redefined posture cone may define a posture space that is effectively the same as the previous posture cone prior the disorientation of the posture state sensor. Accordingly, for the purposes of objectifying the posture state of a patient, information gathered using a previous posture cone should correspond to the information gathered using the redefined posture cone, e.g., as defined by reference coordinate vector and tolerance angle or cosine value, such that there should be no requirement to distinguish between the two types of information for purposes of objectification, or evaluation of posture state information in general. Similarly, for the purposes of objectifying the posture state of a patient, information gathered using one or more prior posture reference vectors, in a manner similar to that described above with regard to FIG. 8C, should correspond to the information gathered using redefined posture reference vectors, such that there should be no requirement to distinguish between the two types of information for purposes of objectification, or evaluation of posture state information in general.

In some examples, more than one posture cone or posture reference vector may be defined for a patient. For example, IMD 14 may store one posture cone that defines an upright posture state to detect when patient 12 is in an upright posture state, another posture cone that defines an a lying right posture state to detect when patient 12 is in a lying right posture state, another posture cone that defines a lying left posture state when patient 12 is in a lying left posture state, another posture cone that defines a lying back posture state, and another posture cones that defines a lying front posture state, and so forth. Depending on the disorientation of the posture state sensor, it may be necessary to redefine each of the posture cones for each of the respective postures or posture reference vectors. Hence, the general process outlined in FIG. 12 may be applied to reorient multiple cones or posture reference vectors. In addition, the process of FIG. 12 may be applied, in some instances, to repeat reorientation multiple times, in the event disorientation is detected multiple times.

One or more techniques may be used to redefine the posture cones corresponding to each patient posture state. For example, individual posture cones may be sequentially redefined by patient 12. In some cases, this may require that patient 12 sequentially occupy each posture state corresponding to the respective posture cones that are being redefined. In some examples, each posture cone may stay active up to the time that it is redefined by a new posture cone. By permitting some posture cones to be defined based on the posture state sensor data in the "old" orientation at the same time as the posture cones based on the posture state sensor data in the current orientation, until all of the posture cones have been redefined, two or more posture cones may overlap for a period. Accordingly, in some cases, IMD 14 may suspend the use of all posture cones to detect patient posture states until each of the posture cones is redefined. However, in some cases, patient 12 may be allowed to redefine individual posture cones while allowing other posture states to remain defined by posture cones that have not been redefined.

Accordingly, in some examples, IMD 14 may contain hierarchal instructions for detecting the posture state of patient 12 when posture state sensor data indicates a sensed coordinate vector that is located in a space of more than one posture cone. For example, in some cases, posture state module 86 may detect the posture state according to the to the most recently defined posture cone, as it may be assumed that the most recently defined posture cone is the most accurate with respect to the actual posture state of patient 12. Using such hierarchal instructions, posture state module 86 may be allowed to detect a patient posture state even if one or more posture cones overlap, e.g., for the reasons previously described.

In other examples, posture state module 86 may automatically reduce the tolerance value of one or more of the overlapping cones such that they no longer overlap. For example, the tolerance value of a posture cone based on the previous sensor orientation may automatically be adjusted to effectively reduce one or more of the posture cones until the cones in question no longer overlap. In this manner, by changing the posture state reference data for "old" posture cone and not changing the tolerance value of the posture state reference data "new" posture cone, once all of the posture cones have been redefined based on the current sensor orientation, these posture cones should more accurately define the posture states of patient 12 as compared to a technique in which the tolerance value of a "new" posture cone may be adjusted. However, in some examples, the tolerance value of the "new" posture cone may also be adjusted such that respective cones do not overlap.

As mentioned, in other examples, all posture cones may be deactivated upon the redefinition of the first posture cone, at which time IMD 14 may not be able to detect the posture state of patient 12 no matter what posture state is actually occupied by patient 12. In some examples, IMD 14 may be configured to detect patient posture states as the individual cones are redefined or, alternatively, IMD 14 may be configured to not use redefined posture cones to detect the posture state of patient 12 until all of the posture cones have been redefined.

While the above examples are described with respect to requiring patient 12 to occupy each of the posture states to define the posture cones corresponding to a respective posture state, in some cases posture state module 86 may automatically redefine one or more of the posture cones using one or more posture cones as a reference cone. For example, posture state module 86 may establish a relative relationship between one or more postures before they are redefined such that the posture state may be reconstructed by simply redefining one or more reference cones. For example, if posture cone A has a known geometric relationship to posture cones X, Y and Z, then it may be possible to redefined the posture state reference data for posture cone A based on the redefined posture state reference data for posture cones X, Y and Z. In this case, patient 12 may occupy pertinent posture states for posture cones X, Y and Z but does not need to occupy the posture state for posture cone A. In this manner, posture state module 86 may redefine one or more posture cones without requiring patient 12 to occupy the posture state corresponding to the posture cone.

As another example, based on the originally defined posture cones or some cones defined thereafter, posture state module 86 may establish the relative position of posture cones with respect to one or more reference cones. For example, for posture cones defined in two-dimensional space, the approximate angle of a posture reference vector, e.g., of a posture cone with respect to another posture reference vector of a reference posture cone may be periodically determined and stored in memory 82 of IMD 14. In some examples, a similar known relationship may be established based on periodically determining one or more cosine values. Using the known relationship, in addition to established tolerance values, posture state module 86 may automatically redefine posture cones once the reference posture cone is redefined. In some cases, a similar technique may be used for posture cones defined in three-dimensional space, e.g., using two or more reference cones. Again, although posture cones are described for purposes of illustration, other posture volumes such as cylinders or the like may be used. In some examples, similar techniques may be used for posture reference vectors in general, such as reference vectors 159, 161, 163, 165 described in FIG. 8C.

In some examples, rather than determining the angular relationship between a posture vector and reference cones, posture state module 86 may analyze the relative spatial difference between the space defined by a redefined posture cone and the space defined by the posture cone it is replacing. For example, using a relative coordinate system, a translation value may be established in each axial direction by analyzing the difference between one or more reference points common to the redefined posture cone and the previous cone. For example, it may be determined that the space of a redefined posture cone has only effectively moved 2 units in one axial direction based on a comparison of the redefined posture cone to the posture cone it is replacing. In such an example, posture state module 86 may automatically translate the remaining posture cones such that they are redefined consistent with the movement of two units in the same axial direction.

Posture state reference data, defining posture cones or other posture volumes, are not limited to being redefined one time but instead may be redefined multiple times. For example, a posture cone that redefined an original posture cone may be further replaced by another redefined cone. In such examples, IMD 14 may associate some or all of the therapy information corresponding to the first redefined cone to the second redefined cone, in addition to therapy information associated with the original posture cone, which may or may not associated with the first redefined cone. Such a function may be accomplished using the data structures previously described, e.g., a look-up table.

FIGS. 13A-13D are conceptual diagrams illustrating example screens that may be displayed by a user interface 232 of a clinician programmer 60 to allow a user, such as, e.g., a clinician, to redefine posture state reference data for one or more posture cones. Again, in some implementations, the posture state reference data may include a posture reference coordinate vector and a tolerance angle or cosine value that defines a volume of vector coordinates that reside within a given posture cone and designate a given posture state, such as upright (or standing), lying back, lying front, lying left, or lying right.

In the example of FIGS. 13A-13D, display 64 of clinician programmer 60 provides screens 234A-234D, respectively, (collectively "screens 234") to the user via user interface 232. Although screens 234A-234D will be described with respect to clinician programmer 60, the same or similar screens may be presented via a user interface of any suitable external programming device, such as, e.g., patient programmer 30 (FIG. 2) or another computing device.

Figures 13A, 13B:
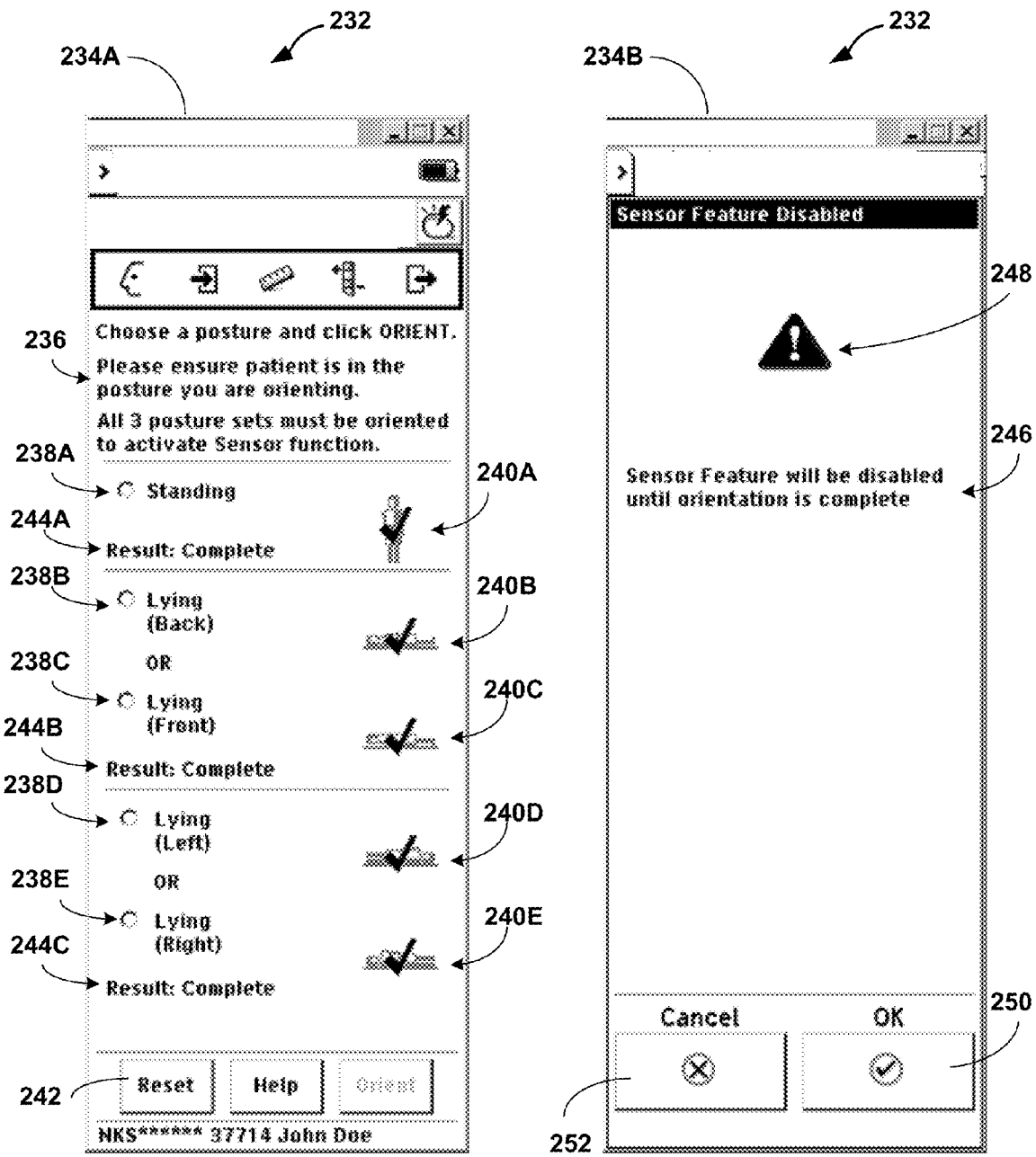
FIGS. 13A-13D are conceptual diagrams illustrating example screens that may be displayed by a user interface to allow a user to redefine one or more posture cones of a patient.

By navigating through screens 234A-234D, a user may be allowed to perform reorientation by redefining the posture state reference data for one or more posture cones used by posture state module 86 of IMD 14 to detect the posture state of a patient. In the example of FIGS. 13A-13B, posture state module 86 is configured to use five posture cones to detect five different posture states of patient 12. The posture states are labeled "Standing," "Lying (Back)," Lying (Front)," "Lying (Left)," and "Lying (Right)," which correspond to the patient posture states indicated by their respective labels. However, screens similar to that of one or more screens 234 may used to redefine one or more different posture cones of patient 12 to detect one or more patient posture states desired to be detected by IMD 14.

Referring to FIG. 13A, screen 234A may be presented to a user to redefine each of the five posture cones. Screen 234A may be presented after the user has communicated to clinician programmer 60 a desire to perform reorientation to redefine posture state reference data for the posture cones, e.g., by selecting an redefinition icon from a drop down menu or an icon contained on a previous screen. Alternatively, screen 234A may be presented automatically by programmer 60 if it is determined, e.g., by IMD 14 or programmer 60, that the posture state sensor of IMD 14 has become disoriented. As previously described IMD 14 may automatically suspend the delivery of stimulation therapy according to the posture state detected if it is determined that the posture state sensor has likely become disoriented. In such an example, patient 12 may be required to navigate through screens 234A-234D before IMD 14 resumes the delivery of stimulation therapy according to the detected posture state of patient 12.

Screen 234A includes instructions text 236 which may display one or more instructions or information to a user with respect to the redefinition process. In this example, instructions text 236 instructs the user how to carry out the reorientation process, referred to by programmer 60 as orienting a posture. In particular, instructions text 236 instructs a user to "Choose a posture and click ORIENT". Further, instructions text 236 conveys to the user that patient 12 should be in the posture that is being oriented, i.e., defined, according to the posture sensor data generated by the posture state sensor at that time.

Furthermore, instructions text 236 conveys to the user that all three posture sets must be oriented to activate the posture state sensor function. In this example, "Sensor function" may refer to the automatic delivery of stimulation therapy by IMD 14 based on the detected posture state of patient 12 using the respective posture cones. As previously described, in some examples, not every posture cone may need to be manually redefined after a posture state sensor has become disoriented, but instead IMD 14 may utilize known properties, such as known spatial or geometric relationships of posture cones with respect to one or more reference posture cones. In this example, IMD 14 is configured to automatically define the "Lying (Back)" posture cone once the "Lying (Front)" posture cone is manually redefined, and vice versa. IMD 14 is also configured similarly with respect to the "Lying (Left)" and "Lying (Right)" posture cones. Accordingly, user interface 234A indicates instructions consistent with this configuration to the user via instructions text 236.

Screen 234A further includes posture selection items 238A-238E (collectively "posture selection items 238"), which correspond to the posture states of "Standing," "Lying (Back)," "Lying (Front)," "Lying (Left)," and "Lying (Right)," respectively. A user may use posture selection item 238 to select the posture state that patient is occupying or will be occupying such that the posture cone for that posture state may be redefined. For example, a user may instruct patient 12 to lie on his or her back. Once patient 12 is lying on his or her back, the user may communicate that they would like to define the "Lying (Back)" posture cone by selecting posture section item 238B, e.g., by clicking next to the posture description with a stylus or other input media.

Screen 234A further includes posture state status indicators 244A-244C to indicate to the user the status of required posture state or group of posture states with respect to the definition process. For example, posture state status indicator 244B corresponds to the two posture cones defining the "Lying (Back)" and "Lying (Front)" posture states. As previously described, IMD 14 is configured to automatically define one of the posture cones once the other is manually defined. Accordingly, when one posture cone is has been manually defined, the related posture cone may also be defined. In this example, since there is an active posture cone defined for each respective posture state, posture state status indicator 244B indicates the status of the "Lying (Back)" and "Lying (Front)" posture group as "Complete." Furthermore, indicators 244A and 244C also indicate the status of the remaining posture groups as "Complete." This is consistent with the fact that the posture cones are being redefined in this example, i.e., posture cones are already defined for each posture state.

Screen 234A also includes posture state status icons 240A-240E. Each respective icon has a graphical component illustrating the posture state that a respective posture icon is related to, e.g., icon 240A includes a graphical component illustrating a human in a standing posture state. In particular, icons 240A-240E correspond to the five posture states previously described. Icons 240A-240E indicate whether a posture cone is defined and active for each posture state, not just for each posture group, as with indicators 244A-244C. In this case, user interface 232 indicates to the user that posture cone is defined for a respective posture state by superimposing a "check-mark" over each posture state illustration. As shown in FIG. 13A, posture state indicator 240A-240E indicate that all posture states are defined by an active posture cone.

Screen 234A also includes "Reset" button 242. To redefine the existing posture cones, e.g., by redefining the posture state reference data for the respective cones, used by IMD 14 to detect the posture states of patient 12, a user may select the Reset button 242 to communicate to programmer 60 that they desire to redefine the existing posture cones for the respective patient posture states.

Referring to FIG. 13B, a user may navigate from screen 234A to screen 234B after user attempts to redefine the posture cone for a selected posture state by selecting the "Reset" button 242 of screen 234A. Screen 234B allows programmer 60 to confirm that the user desires to proceed with the posture cone definition process for the posture state selected in screen 234A. Screen 234B includes text section 246 and warning icon 248. Text section 246 includes textual information informing the user that the proposed action will suspend the delivery of stimulation based on the detected posture state of patient by IMD 14.

Warning icon 248 alerts the user to the relative importance of the action they are about to undertake. If the user wishes to continue with the redefinition process, they may proceed by selecting "OK" button 250 on screen 234B. At that point, programmer 60 will suspend the delivery of stimulation by IMD 14 to patient 12 based on the detected posture state. Conversely, if the user elects to abort the redefinition process, the user may select "Cancel" button 252 on screen 234B. At that point, programmer 60 may return to a default screen or indicate to the user that the redefinition process was aborted and that IMD 14 will continue to deliver posture-responsive therapy based on the posture state detected using the existing posture cones.

Figures 13C, 13D:
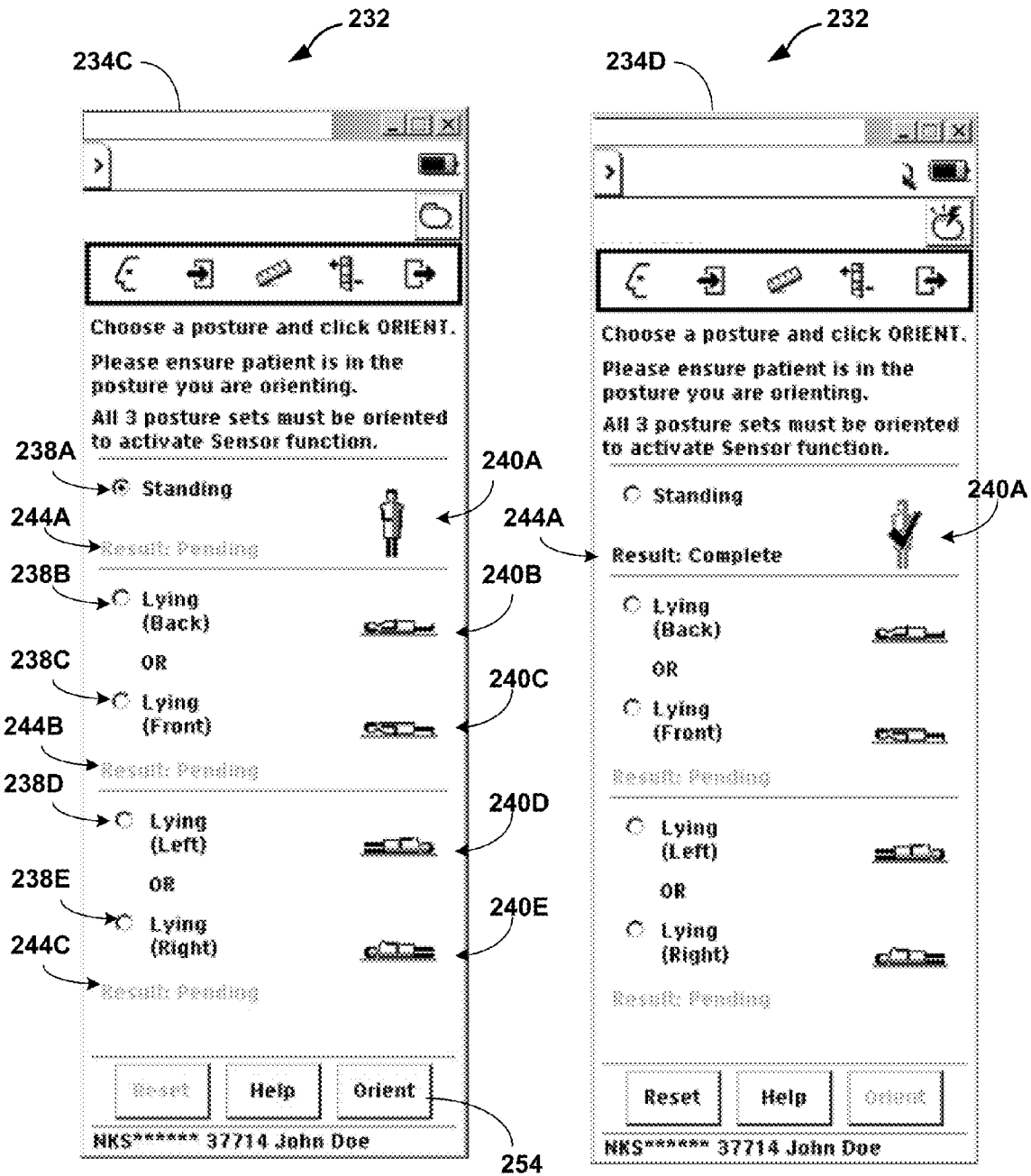

Referring to FIG. 13C, a user may navigate from screen 234B to screen 234C by selecting "OK" button 250 on screen 234B. Screen 234C is similar to screen 234A, at least to the extent that screen 234C includes posture selection items 238A-238E, posture state status indicators 244A-244C, posture state status icons 240A-240E, and instructions text 236, as also included in screen 234A. However, unlike screen 234A, the icons 240A-240E no longer indicate that a posture cone is defined and/or active for the posture states indicated by the icons. Instead, icons 240A-240E indicate to the user that there no posture cones defined and/or active for the respective posture states by not superimposing check-marks over the posture state illustration in any of icons 240A-240E.

Furthermore, posture state status indicators 244A-244C no longer indicate that the status of required posture state or group of posture states with respect to the definition process is "Complete." Instead, all of the posture state status 244A-244C indicate that the definition process of each of the required groups is "Pending." Accordingly, the user is informed that all three groups that are required to redefine the respective postures cones have yet to be completed.

To complete one of the three groups required for the redefinition process, a user must first select one posture state contained in the group desired to complete. Once a user has selected a respective posture state via posture selection items 238, "Orient" button 254 may become active, e.g., the text of the button 254 may darken (not shown). When button 254 is active, button 254 may be selected by the user to communicate to IMD 14 that the posture cone of the selected posture state should be defined. In screen 234C, the user has selected that a posture cone be defined for the "Standing" posture state, as indicated by the partially filled posture selection item 238A.

The user may navigate from screen 234C to screen 234D by selecting the "Orient" button 254 while a posture state is selected via posture selection items 238A-238E. Once the "Orient" button is selected by the user, programmer 60 may communicate to IMD 14 that posture state module 86 should begin analyzing the posture sensor data being received from the posture state sensor such that the posture state reference data, e.g., reference coordinate vector, for the posture cone corresponding to the posture state may be redefined, and also may communicate that posture state selected by the user so it may correctly associate the posture cone with the selected posture state.

Once IMD 14 has redefined the posture state reference data for posture cone corresponding to the posture state selected by the user, programmer 60 may indicate to the user that the posture cone has been successfully redefined. As shown, screen 234D includes posture state status indicator 244A which indicates the group containing the standing posture state is "Complete." Furthermore, screen 234D includes posture state status icons 240A, which indicates that posture cone is defined for the standing posture state by superimposing a check-mark over the posture state illustration.

The user may complete the redefinition process by redefining by repeating the described process for either the "Lying (Back)" or "Lying (Front)" posture state, and either the "Lying (Left)" or "Lying (Right)" posture state. At that time, all five posture states will have corresponding posture cones that have been redefined, and user interface 232 may display a screen similar to that of screen 234A. In this manner, a user may redefine posture cones corresponding to posture states of patient 12. Once redefined, IMD 14 may use the posture cones to detect the posture state of patient 12 and deliver therapy based on the detected posture state.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
receiving first posture sensor data from a posture state sensor when a patient occupies a first posture state during a first period of time;
defining posture state reference data corresponding to the first posture state based at least in part on the first posture sensor data; and
redefining the posture state reference data based on second posture sensor data from the posture state sensor when the patient subsequently occupies the first posture state during a second period of time after the first period of time, wherein at least one of the receiving, defining, and redefining is performed at least in part via one or more processors.

2. The method of claim 1, wherein the posture state reference data defines at least one of a posture volume or posture area.

3. The method of claim 2, wherein the posture volume comprises a posture cone, and wherein the posture state reference data includes a posture reference coordinate vector and a tolerance angle that define the posture cone.

4. The method of claim 2, wherein the posture state reference data comprises a posture reference coordinate vector and at least one cosine value.

5. The method of claim 2, wherein the posture volume comprises a posture donut, and wherein the posture state reference data includes a posture reference coordinate vector and at least one of a range of cosine values or range of angles that define the posture donut.

6. The method of claim 5, wherein the posture state reference data includes a plurality of posture state reference vectors associated with the posture donut.

7. The method of claim 6, wherein the posture state reference coordinate vector comprises a virtual posture state reference coordinate vector, the virtual posture state reference vector defined based at least in part on the plurality of posture state reference vectors associated with the posture donut.

8. The method of claim 1, further comprising associating therapy information with the defined posture state reference data, and subsequently associating at least some of the therapy information with the redefined posture state reference data.

9. The method of claim 8, wherein the therapy information comprises therapy objectification information and parameter information.

10. The method of claim 9, wherein the parameter information comprises different therapy parameter values for therapy delivered when the patient occupies different posture states.

11. The method of claim 8, wherein the therapy information comprises one or more adjustments to posture state reference data made subsequent to defining the posture state reference data.

12. The method of claim 8, wherein the therapy information comprises a tolerance value defined for the posture state reference data prior to redefining the posture state reference data,
wherein redefining the posture state reference data comprises redefining a posture reference coordinate vector, and
wherein subsequently associating the therapy information with the redefined posture state reference data comprises associating the tolerance value defined for the posture state reference data prior to redefining the posture state reference data with the redefined posture reference coordinate vector to redefine to the posture state reference data.

13. The method of claim 1, further comprising receiving the second posture sensor data from the posture state sensor when the patient subsequently occupies the first posture state during the second time period after the first period of time.

14. The method of claim 1, further comprising:
detecting the posture state of the patient based on the posture state reference data; and
delivering therapy to the patient from a medical device according to the detected posture state of the patient.

15. The method of claim 1, further comprising detecting that the posture state sensor has been disoriented after defining the posture state reference data, wherein redefining comprises redefining the posture state reference data in response to the detecting that the posture state sensor has been disoriented.

16. The method of claim 15, wherein detecting that the posture state sensor has been disoriented comprises automatically detecting that the posture state sensor has been disoriented based at least in part on posture sensor data received from the posture state sensor.

17. The method of claim 15, further comprising:
delivering therapy to the patient from a medical device according to the posture state determined based on the posture state reference data; and
subsequently suspending the delivery of therapy to the patient in response to the detection that the posture state sensor has been disoriented, wherein the therapy delivery is suspended until the posture state reference data has been redefined.

18. The method of claim 1, wherein the posture state reference data comprises first posture state reference data, the method further comprising:
receiving third posture sensor data from the posture state sensor when the patient occupies a second posture state during a third period of time;
defining second posture state reference data corresponding to the second posture state based at least in part on the third posture sensor data; and
redefining the second posture state reference data.

19. The method of claim 18, wherein the second posture state reference data is redefined based on fourth posture sensor data from the posture state sensor when the patient subsequently occupies the second posture state during a fourth period of time.

20. The method of claim 18, wherein the second posture state reference data is redefined based on the redefined first posture state reference data.

21. The method of claim 18, further comprising detecting the second posture state of the patient based on the second posture state reference data after the first posture state reference data has been redefined.

22. The method of claim 1, further comprising:
subsequently redefining the previously redefined posture state reference data based on third posture sensor data from the posture state sensor when the patient subsequently occupies the first posture state during a third period of time.

23. A system comprising:
a posture state sensor configured to generate first posture sensor data when a patient occupies a first posture state during a first period of time; and
a processor configured to define posture state reference data corresponding to the first posture state based at least in part on the first posture sensor data, and redefine the posture state reference data based on second posture data generated by the posture state sensor when the patient subsequently occupies the first posture state during a second period of time after the first period of time.

24. The system of claim 23, wherein the posture state reference data defines a posture volume.

25. The system of claim 24, wherein the posture volume comprises a posture cone, and wherein the posture state reference data includes a posture coordinate vector and a tolerance angle that define the posture cone.

26. The system of claim 24, wherein the posture state reference data comprises a posture reference coordinate vector and at least one cosine value.

27. The system of claim 24, wherein the posture volume comprises a posture donut, and wherein the posture state reference data includes a posture reference coordinate vector and at least one of a range of cosine values or range of angles that define the posture donut.

28. The system of claim 27, wherein the posture state reference data includes a plurality of posture state reference vectors associated with the posture donut.

29. The system of claim 28, wherein the posture state reference coordinate vector comprises a virtual posture state reference coordinate vector, the virtual posture state reference vector defined based at least in part on the plurality of posture state reference vectors associated with the posture donut.

30. The system of claim 23, wherein the processor is configured to associate therapy information with the defined posture state reference data, and subsequently associate at least some of the therapy information with the redefined posture state reference data.

31. The system of claim 30, wherein the therapy information comprises therapy objectification information and parameter information.

32. The system of claim 31, wherein the parameter information comprises different therapy parameter values for therapy delivered when the patient occupies different posture states.

33. The system of claim 30, wherein the therapy information comprises one or more adjustments to posture state reference data made subsequent to defining the posture state reference data.

34. The system of claim 30, wherein the therapy information comprises a tolerance value defined for the posture state reference data prior to redefining the posture state reference data,
wherein the processor is configured to redefine a posture reference coordinate vector to redefine the posture state reference data, and associate the tolerance value defined for the posture state reference data prior to redefining the posture state reference data with the redefined posture reference coordinate vector to subsequently associate the therapy information with the redefined posture state reference data.

35. The system of claim 23, wherein the posture state sensor generates the second posture sensor data when the patient subsequently occupies the first posture state during the second time period after the first time period.

36. The system of claim 23, further comprising a therapy module configured to deliver therapy to a patient according to a detected posture state of the patient,
wherein the processor is configured to detect the posture state of the patient based on the posture state reference data.

37. The system of claim 23, wherein the processor in configured to detect that the posture state sensor has been disoriented after defining the posture state reference data, wherein the processor redefines the posture state reference data in response to the detecting that the posture state sensor has been disoriented.

38. The system of claim 37, wherein the processor is configured to automatically detect that the posture state sensor has been disoriented based at least in part on posture sensor data received from the posture state sensor.

39. The system of claim 37, further comprising a therapy module configured to deliver therapy to the patient according to the posture state detected by the processor based on the posture state reference data,
wherein the processor is configured to subsequently suspend the delivery of therapy to the patient from the therapy module in response to the detection that the posture state sensor has been disoriented, wherein the processor is configured to suspend delivery of the therapy until the posture state reference data has been redefined.

40. The system of claim 23, wherein the posture state reference data comprises first posture state reference data,
wherein the processor is configured to receive third posture sensor data from the posture state sensor when the patient occupies a second posture state during a third period of time, define second posture state reference data corresponding to the second posture state based at least in part on the third posture sensor data, and redefine the second posture state reference data.

41. The system of claim 40, wherein the processor is configured to redefine the second posture state reference data based on fourth posture sensor data received from the posture state sensor when the patient subsequently occupies the second posture state during a fourth period of time.

42. The system of claim 40, wherein the processor is configured to redefine the second posture state reference data based on the redefined first posture state reference data.

43. The system of claim 40, wherein the processor is configured to detect the second posture state of the patient based on the second posture state reference data after the first posture reference data has been redefined.

44. The system of claim 23, wherein the processor is configured to redefine the previously redefined posture state reference data based on third posture sensor data from the posture state sensor when the patient subsequently occupies the first posture state during a third period of time.

45. The system of claim 23, wherein the processor resides in at least one of an implantable medical device or external programmer.

46. A computer-readable storage medium comprising instructions for causing one or more processors to:
receive first posture sensor data from a posture state sensor when a patient occupies a first posture state during a first period of time;
define posture state reference data corresponding to the first posture state based at least in part on the first posture sensor data; and
redefine the posture state reference data based on second posture sensor data from the posture state sensor when the patient subsequently occupies the first posture state during a second period of time after the first period of time.

47. A system comprising:
means for receiving first posture sensor data from means for sensing posture state data when a patient occupies a first posture state during a first period of time;

means for defining posture state reference data corresponding to the first posture state based at least in part on the first posture sensor data; and means for redefining the posture state reference data based on second posture sensor data from the posture state sensor when the patient subsequently occupies the first posture state during a second period of time after the first period of time.

48. The method of claim 1, further comprising:

detecting, prior to the redefining the posture state reference data, a posture state of the patient based on the posture state reference data;

delivering therapy to the patient based on the posture state of the patient detected based on the posture state reference data;

subsequently detecting, after the redefining the posture state reference data, the posture state of the patient based on the redefined posture state reference data; and delivering therapy to the patient based on the posture state of the patient detected based on the redefined posture state reference data.

49. The system of claim 23, wherein the processor is configured to detect, prior to the redefining the posture state reference data, a posture state of the patient based on the posture state reference data, control delivery of therapy to the patient based on the posture state of the patient detected based on the posture state reference data, subsequently detect, after the redefining the posture state reference data, the posture state of the patient based on the redefined posture state reference data, and control delivery of therapy to the patient based on the posture state of the patient detected based on the redefined posture state reference data.

50. The system of claim 23, further comprising:

an implantable medical device including the posture state sensor; and an external programmer.

* * * * *